US 6,419,954 B1
United States Patent
Chu et al.
(10) Patent No.: US 6,419,954 B1
(45) Date of Patent: Jul. 16, 2002

(54) TABLETS AND METHODS FOR MODIFIED RELEASE OF HYDROPHILIC AND OTHER ACTIVE AGENTS

(75) Inventors: James S. Chu, Palo Alto; Yisong Yang, Sunnyvale; Joseph A. Fix, Half Moon Bay, all of CA (US)

(73) Assignee: Yamanouchi Pharmaceutical Co., Ltd. (JP)

( * ) Notice: Subject to any disclaimer, the term of this patent is extended or adjusted under 35 U.S.C. 154(b) by 0 days.

(21) Appl. No.: 09/599,102

(22) Filed: May 19, 2000

(51) Int. Cl.$^7$ .............................. A61K 9/20; A61K 9/22; A61K 9/36

(52) U.S. Cl. ........................ 424/465; 424/457; 424/490; 424/476; 424/441; 424/461

(58) Field of Search ................. 424/465, 490, 424/457, 441, 476, 469, 461

(56) References Cited

U.S. PATENT DOCUMENTS

| | | | |
|---|---|---|---|
| 4,404,183 A | 9/1983 | Kawata et al. ............. 424/19 |
| 4,764,378 A | 8/1988 | Keith et al. ............... 424/435 |
| 4,806,337 A | 2/1989 | Snipes et al. .............. 71/65 |
| 5,273,758 A | 12/1993 | Royce ...................... 424/465 |
| 5,322,655 A | 6/1994 | Ebey ....................... 264/40.5 |
| 5,370,879 A | * 12/1994 | Masterson et al. ......... 424/490 |
| 5,766,623 A | * 6/1998 | Ayres et al. ............... 424/441 |
| 5,846,563 A | * 12/1998 | Baichwal ................... 424/457 |
| 5,908,638 A | * 6/1999 | Huber et al. .............. 424/465 |
| 5,945,125 A | 8/1999 | Kim ........................ 424/473 |
| 6,024,982 A | * 2/2000 | Oshlack et al. ............ 424/476 |

FOREIGN PATENT DOCUMENTS

| | | | |
|---|---|---|---|
| EP | 0661045 A1 | 5/1995 | ........... A61K/9/22 |
| WO | WO 94/06414 | 3/1994 | ........... A61K/9/22 |
| WO | WO 98/56359 | 12/1998 | ........... A61K/9/22 |

OTHER PUBLICATIONS

Chiu, H.–C. et al.: "Synthesis and characterization of pH–sensitive dextran hydrogels as a potential colon–specific drug delivery system" J. Biomater, Sci Polymer Edu., 10(5):591–608 (1999).

Ertan, G. et al.: "Sustained–released microcapsules of nitrofurantoin and amoxicillin; preparation, in–vitro release rate, kinetic and micromeritic studies" J. Microencapsulation, 14(3):379–388 (1997).

Chu, J. S. et al.: "Effect of different physical modification on drug release kinetics from a hydrophilic controlled–released matrix" Proceed. Int'l. symp. Control Rel. Bioact. Mater., 25:898–899 (1998).

Hu, Zhaopeng et al.: "New preparation method of intestinal pressure–controlled colon delivery capsules by coating machine and evaluation in beagle dogs" Journal of Controlled Release, 56: 293–302 (1998).

Heinämäki, Jyrki et al.: "Optimization of Aqueous–Based Film Coating of Tablets Performed by a Side–Vented Pan–Coating System" Pharmaceutical Development and Technology, 2(4):357–364 (1997).

Iga, Yoshinori et al.: "(±)–cis–2–Methylspiro[1,3–oxathiolane–5,3'–quinuclidine] Hydrochloride, Hemihydrate (SNI–2011, Cevimline Hydrochloride) Induces Saliva and Tear Secretions in Rats and Mice: The Role of Muscarinic Acetylcholine Receptors" Japan J. Pharmacol., 78:373–380 (1998).

(List continued on next page.)

Primary Examiner—Jose' G. Dees
Assistant Examiner—Mina Haghighatian
(74) Attorney, Agent, or Firm—Townsend and Townsend and Crew LLP

(57) ABSTRACT

The invention provides a tablet and methods for making the tablet comprising a gel-forming material and at least one particle comprising an active agent in contact with a coating material to modify release of the active agent.

53 Claims, 11 Drawing Sheets

OTHER PUBLICATIONS

Ishibashi, T. et al.: "Evaluation of colonic absorbability of drugs in dogs using a novel colon–targeted delivery capsule (CTDC)"Journal of Controlled Release, 59:361–376 (1999).

Iwabuchi, Y. et al.: "Salivary Secretion and Histopathological Effects after Single Administration of the Muscarinic Agonist SNI–2011 in MRL/lpr. Mice" ARCH. INT. PHARMACODYN, 328:315–325 (1994).

Iwabuchi, Y. et al.: "Sialogogic Activities of SNI–2011 Compared with those of Pilocarpine and McN–A–343 in Rat Salivary Glands: Identification of a Potential Therapeutic Agent for Treatment of Sjörgen's Syndrome" Gen. Pharmac., 25(1):123–129 (1994).

Jambhekar, S. S. et al.: "pH–and Flow–Rate–Independent Release of Drug from Uncoated Slow–Release Tablets" Journal of Pharmaceutical Science, 74(9):991–994 (1985).

Jona, Kaori et al.: "Preparation of Lecithin Microcapsules by a Dilution Method Using the Wurster Process for Intraarterial Administration in Gadolinium Neutron Capture Therapy" Chem. Pharm. Bull., 47(1):54–63 (1999).

Krögel, I. et al.: "Pulsatile Drug Release from an Insoluble Capsule Body Controlled by an Erodible Plug" Pharmaceutical Research, 15(3):474–481 (1998).

Leopold, C.S.: "Coated dosage forms for colon–specific drug delivery" Research Focus, 2(5):197–203 (1999).

Macleod, G. S. et al.: "The potential use of mixed films of pectin, chitosan and HPMC for bimodal drug release" Journal of Controlled Release, 58:303–310 (1999).

Mandal, T.K.: "Evaluation of a Novel Phase Separation Technique for the Encapsulation of Water–Soluble Drugs in Biodegradable Polymer" Drug Development and Industrial Pharmacy, 24(7):623–629 (1998).

Miyamoto, M. et al.: "Design and Preparation of Gadolinium–Reservoir Microcapsules for Neutron–Capture Therapy by Means of the Wurster Process" Chem.Pharm.Bull., 45(12):2043–2050 (1997).

Niwa, K. et al.: "Preparation and Evaluation of a Time–Controlled Release Capsule Made of Ethylcellulose for Colon Delivery of Drugs" Journal of Drug Targeting, 3:83–89 (1995).

Ramdas, M. et al.: "Alginate Encapsulated Bioadhesive Chitosan Microspheres for Intestinal Drug Delivery" Journal of Biomaterials Applications, 13:290–296 (1999).

Sahoo, S.K. et al.: "pH–and Thermo–sensitive Hydrogel Nanoparticles" Journal of Colloid and Interface Science, 206:361–368 (1998).

Sako, K. et al.: "Relationship Between Gelation Rate of Controlled–release Acetaminophen Tablets Containing Polyethylene Oxide and Colonic Drug Release in Dogs" Pharmaceutical Research, 13(4):594–598 (1996).

Tuncel, T. et al.: "In vitro and in vivo studies on microcapsules and tabletted microcapsules of cephradine"Pharmazie, 51(3):168–171 (1996).

Van Bommel, E.M.G. et al., "Comparision of in vivo and in vivo release characteristics of acetaminophen from gradient matrix systems" Biopharmaceutics & Drug Disposition, 12:367–373 (1991).

Yang, L. et al.: "Determination of Continuous Changes in the Gel Layer Thickness of Poly(ethylene oxide) and HPMC Tablets Undergoing Hydration: A Texture Analysis Study" Pharmaceutical Research, 15(12):1902–1906 (1998).

* cited by examiner

US 6,419,954 B1

TABLETS AND METHODS FOR MODIFIED RELEASE OF HYDROPHILIC AND OTHER ACTIVE AGENTS

CROSS-REFERENCES TO RELATED APPLICATIONS

Not Applicable.

STATEMENT AS TO RIGHTS TO INVENTIONS MADE UNDER FEDERALLY SPONSORED RESEARCH AND DEVELOPMENT

Not Applicable.

BACKGROUND OF THE INVENTION

A variety of hydrogel-type preparations have been developed to effect the sustained release of orally ingested drugs. For example, Japanese patent application JP-A-62-120315 discloses a preparation obtained by compression-molding a drug, a hydrogel-forming water-soluble polymer and an enteric coating. JP-A-63-215620 discloses a hydrogel-type preparation with a core having a drug and a water-soluble polymer and an outer layer with a water-soluble polymer as a base. JP-B-40-2053 discloses a sustained-release preparation having a mixture of a drug and a high polymer of ethylene oxide and, as an optional component, a hydrophilic substance. However, all of these preparations are designed to release a drug continuously while the administered preparation is still retained in the upper digestive tract, typically in the stomach and small intestine. They were not intended to provide for a release of a drug in the lower digestive tract including the colon, where little water is available.

Hydrophilic gel-forming preparations have been further developed so that they can provide a sustained release of orally ingested drugs throughout the digestive system, including in the lower digestive tract. For example, EP 0 661 045 describes a preparation adapted to absorb water into its core to undergo substantially complete gelation during its stay in the upper digestive tract. As the tablet moves down the digestive system in the form of a gel to the lower digestive tract, the preparation swells and the gelled outer surface of the tablet erodes gradually releasing the drug. This type of oral tablet is capable of providing a sustained release of the drug throughout the digestive tract, including in the colon.

While the gel-forming preparations, such as those described in the EP 0 661 045, have many applications, they may not be suitable for certain types of active agents, particularly when the active agents are unstable in the gel-forming preparations or may be released in a manner that is not desirable. Thus, there exists a continuing need for improved forms of sustained release preparations which can continuously release an active agent throughout the digestive tract, regardless of the physical or chemical properties of the active agent. Moreover, many situations may require that an active agent be delivered to the patient in a non-random or pulsatile manner, or, that the active agent be delivered to a particular anatomic compartment, e.g., the colon. For example, if an easily degradable drug or a drug with a short biological half-life needs to be delivered to the colon, it cannot be released in the upper digestive tract. Thus, there is a need for tablets that are capable of providing delayed and/or pulsatile release of an active agent. The present invention fulfills these and other needs.

SUMMARY OF THE INVENTION

The present invention provides, for the first time, a tablet and methods for making the tablet that comprises a gel-forming material and at least one particle comprising an active agent in contact with a coating material to modify release of the active agent from the tablet. These particles that comprise the active agent and the coating material are also referred to as "active agent-containing particle", "coated particle" or "coated bead." The gel-forming material forms a matrix (a "gel-forming matrix") for the active agent-containing particles. The active agent-containing particle is formulated with a coating material so that it can modify or control the release of the active agent by, for example, slowing or inhibiting the passage of the active agent out of the tablet and into the digestive system. These tablets are also referred to as OCAS™ (oral controlled absorption system) matrix tablets herein.

In some embodiments of the invention, the release of the active agent from the tablet can be modified and controlled by the combination of two systems: 1) the gel-forming matrix; and 2) the coating material in contact with the active agent. In the digestive system, the gel-forming matrix absorbs water to undergo substantially complete gelation during its stay in the upper digestive tract and moves down into the lower digestive tract undergoing constant erosion, continuously releasing the active agent-containing particles from the tablet. This erosion of the gel-forming matrix can control the release of the active agent-containing particles from the tablet. In addition to the gel-forming matrix, the coating material that is on or around the active agent provides another level of control in releasing the active agent from the tablet. For example, the coating material can modify or control the rate of diffusion of the active agent through the gel matrix and out of the tablet. Moreover, since the coating material provides a physical and/or chemical barrier for the active agent, any type of active agents can be included in the tablets of the present invention. The selection of the active agent is not restricted to those which are released from the tablet in a favorable manner.

In one aspect, the invention is particularly useful for an active agent that is hydrophilic. In the case of water insoluble or less hydrophilic active agents, the erosion of the gel-forming matrix of the tablet precedes the diffusion of the active agent through the swollen gel layer of the tablet. Thus, the active agent release rate limiting step is typically the erosion of the gel-forming matrix. Therefore, with these active agents, the gel-forming matrix alone can provide enough control on release of the active agent and can be used to design a sustained release of these active agents over, e.g., 12–24 hours. However, a hydrophilic active agent tends to diffuse out from the gel-forming matrix faster than the erosion of the swollen gel layer of the tablet. Thus, while a tablet comprising a gel-forming matrix may be useful for water insoluble or less hydrophilic active agents, the gel-forming matrix may not provide for sufficient controlled release for the hydrophilic active agent.

FIG. 9 illustrates this diffusion problem for a hydrophilic active agent. As will be described in further detail below in Example 6B, a tablet comprising Cevimeline HCl (having a high water solubility of about 766 mg/ml at 25° C.) and a gel-forming matrix comprising a polyethylene oxide polymer (PEO) and a polyethylene glycol (PEG) was prepared. The active agent Cevimeline HCl as purchased (without further treatment) was mixed with the gel-forming material. FIG. 9 shows the drug release profile from this conventional Cevimeline HCl matrix tablet. As shown in FIG. 9, substantially all of the drug was released in about 6–8 hours from the tablet. The tablet did not provide for sustained release of the drug over, e.g., 12–24 hours.

Thus, in the embodiments of the invention, a hydrophilic active agent, such as Cevimeline HCl, is physically and/or chemically modified to control its release rate from the tablet. Preferred embodiments of the invention provide a tablet comprising a gel-forming material and a particle comprising a hydrophilic active agent, wherein the particle is formulated to modify release of the active agent from the tablet. For example, the particle comprises a hydrophilic active agent in contact with a coating material (e.g., on or around the active agent). The coating material can slow or prevent the diffusion of the hydrophilic active agent out of the gel-forming matrix.

An improvement in the release profiles of a hydrophilic drug from tablets according to embodiments of the invention are described in Example 6C and shown in FIG. 10. Example 6C describes an embodiment of the present tablet which comprises Cevimeline HCl in contact with a coating material in a gel matrx. As shown in FIG. 10, the release profiles of this modified Cevimeline HCl from the gel matrix tablet are much more gradual and linear than the release profile of unmodified Cevimeline HCl from the conventional matrix tablet shown in FIG. 9. Moreover, when FIGS. 9 and 10 are compared, it is clear that embodiments of the invention can provide a sustained release of a hydrophilic drug up to, e.g., 12–24 hours, compared to conventional gel matrix tablets without modification of the active agent.

While the above example illustrates the use of the embodiments of the invention with a hydrophilic active agent, any suitable active agents, including a less hydrophilic active agent or a hydrophobic active agent, can be incorporated into embodiments of the invention. For example, embodiments of the invention are particularly useful for active agents that are unstable, or sensitive to moisture or oxidation. As an illustration, if the active agent is an enzyme, it may lose its activity if it is in contact with water or the gel-forming material for a prolonged period of time. By providing a physical and/or chemical barrier (e.g., a coating) on or around the active agent, the active agent is protected until it is released from the tablet to the body.

As described above, these embodiments of the invention are capable of sustaining the efficacy of active agents for a prolonged period. One beneficial result is that the number of administrations can be reduced. For example, an individual needs to take a tablet comprising an active agent, such as a drug, only once a day or twice a day. In some cases, tablets can release a drug too quickly into the upper digestive tract of a person, resulting in undesirable side effects. Embodiment of the invention is capable of providing a constant concentration of the drug within the blood of a person. This may reduce potential side effects of the drug by suppressing rapid increases in blood concentration of the drug.

In another aspect, the invention provides tablets and methods for making the tablets that can achieve programmable drug release profiles. For example, the tablets can be designed to have pulsatile, delayed onset or any suitable predetermined release profile. In one embodiment, this is achieved by designing a multilayered tablet. For example, different layers of the multilayered tablet can comprise different active agents, different amounts of active agent and/or different forms of active agent. In another example, different layers of the multilayered tablet can comprise different proportions of a polymer and a gelation facilitator agent, and/or different kinds of a polymer or a gelation facilitator agent. These embodiments provide additional control of the release of the active agents from the tablet. Thus, as the multilayered tablet slowly dissolves in its passage through the digestive tract, it releases varying amounts of active agent (or different active agents) at different times, i.e., in different anatomical compartments (e.g., small intestine versus colon). This effectively allows a programmable active agent release scheme. For example, it may be desirable to release larger amounts of active agent initially (to be absorbed, e.g., in the stomach or upper end of the small intestine) while gradually releasing diminishing amounts of active agent release as the tablet passes through to the end of the colon (or vice versa). Alternatively, it may be desirable that an active agent only be released in the colon. In another embodiment, one active agent (or form of the active agent) is released in the upper digestive tract (e.g., stomach or small intestine) and another active agent or a variation of the active agent is released in the lower digestive tract (e.g., large intestine or colon).

Accordingly, in one aspect, the invention provides a tablet comprising: at least one particle comprising a hydrophilic active agent in contact with a coating material to modify release of the active agent, and a gel-forming material comprising: a polymer; and a gelation facilitator agent having a solubility higher than about 0.1 gram/ml in water at a temperature of about 20° C.

In one embodiment, the particle comprises an active agent and a coating material on or around the active agent.

In another embodiment, the hydrophilic active agent has a water solubility of at least about 30 mg/ml at a temperature of about 25° C.

In yet another embodiment, the hydrophilic active agent is a quinuclidine derivative or acetylcholine.

In yet another embodiment, the active agent-containing particle has a size between about 50 µm to about 5 mm, preferably between about 100 µm to about 3 mm, and more preferably between about 300 µm to about 2 mm.

In yet another embodiment, the tablet comprises a plurality of the active agent-containing particles and wherein the gel-forming material forms a matrix for the plurality of the particles.

In yet another embodiment, the active agent is in the form of a crystal or a granule, and/or the particle comprises a plurality of active agent crystals or granules.

In yet another embodiment, the coating material slows release of the active agent from the tablet.

In yet another embodiment, the coating material is flexible.

In yet another embodiment, the coating material is selected from the group consisting of a natural polymer, a semi-synthetic polymer, and a synthetic polymer. Examples of these polymers include chitosan, methylcellulose, ethylcellulose, hydroxyethylcellulose, hydroxypropylcellulose, hydroxyethylmethylcellulose, hydroxypropylmethylcellulose, cellulose acetate membrane, cellulose acetate butyrate, cellulose acetate propionate, cellulose acetate phthalate, hydroxypropylmethylcellulose phthalate, polyacrylic acid, polyvinyl acetate, poly(vinylacetate phthalate), poly(vinyl alcohol), poly(vinyl pyrrolidone), poly(lactic acid), poly(glycolic acid), poly(lactic/glycolic acid), poly(dimethyl silicone), poly(hydroxyethyl methacrylate), poly(ethylene/vinyl acetate), poly(ethylene/vinyl alcohol), or a mixture thereof.

In yet another embodiment, the coating material further comprises a plasticizer, a stabilizer or both.

In yet another embodiment, the polymer comprises a polyethylene oxide polymer.

In yet another embodiment, the gelation facilitator agent comprises a polyethylene glycol.

In yet another embodiment, the polymer to the gelation facilitator ratio is between about 1:9 to about 9:1 by weight, preferably between about 3:7 to about 7:3 by weight, more preferably between about 4:6 to about 6:4 by weight.

In yet another embodiment, the tablet has a hardness of at least about 2 kp.

In yet another embodiment, the tablet has a hardness between about 2 kp and about 10 kp.

In yet another embodiment, the tablet provides a sustained release of the active agent for at least about 12 hours.

In yet another embodiment, the tablet further comprises a non-hydrophilic active agent.

In yet another embodiment, the tablet comprises at least two different types of particles with different active agents.

In yet another embodiment, the particles in the tablet comprise at least two different types of particles with different coating materials.

In yet another embodiment, the distribution of the particles in the tablet is non-random.

In yet another embodiment, the tablet is a multilayered tablet.

In yet another embodiment, at least two of the layers of the multilayered tablet comprise a different amount of the particles or at least two different types of active agents.

In yet another embodiment, the particles in the tablet are concentrated at the core of the tablet.

In yet another embodiment, the polymer comprises a polyethylene oxide polymer and the gelation facilitator agent comprises a polyethylene glycol.

In another aspect, the invention provides a method for producing a modified tablet, the method comprising: (1) mixing a formulation comprising: (a) at least one particle comprising a hydrophilic active agent in contact with a coating material to modify release of the active agent; (b) a polymer; and (c) a gelation facilitator agent having a solubility higher than about 0.1 gram/ml in water at a temperature of about 20° C.; and (2) compressing the formulation to produce the tablet. In these methods, any of the materials described herein can be used to produce a tablet. For example, in one embodiment of the methods, the particle comprises the active agent and a coating material on the active agent. In another example, the coating material is flexible so that it does not crack during compressing the formulation into the tablet. In yet another example, the coating material is hydrophobic.

In one embodiment of the methods, the particle is produced by spraying the coating material on the active agent.

In another embodiment, the polymer is granulated with the gelation facilitator agent in step (1).

In yet another embodiment, the polymer and the gelation facilitator agent are granulated with the active agent-containing particles in step (1).

These and other aspects of the present invention will become apparent to those skilled in the art from the following detailed description of the invention, the accompanying drawings, and the appended claims.

DEFINITIONS

Figure 1A:
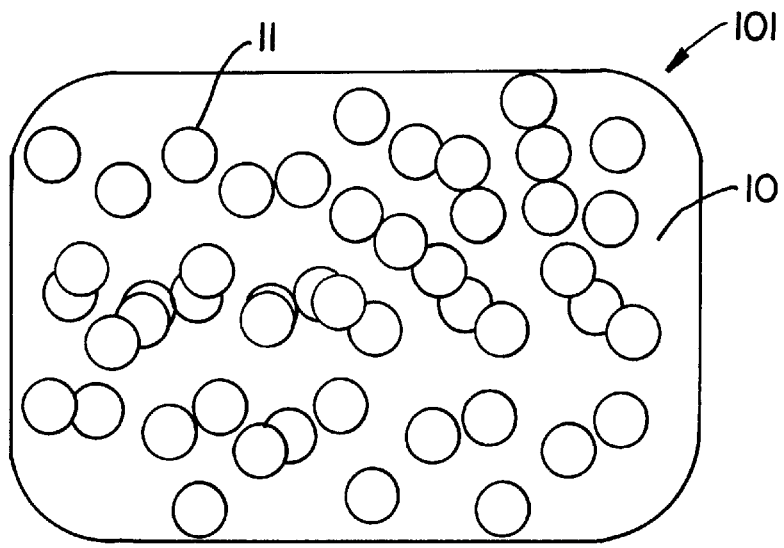
FIG. 1A illustrates one embodiment of tablet 101 comprising a gel-forming matrix 10 and particles 11, wherein the particles comprise an active agent and a coating material in contact with the active agent.

"A sustained release tablet" refers to a tablet which is capable of releasing an active agent to the body for a prolonged period of time, e.g., for at least about 8 hours, preferably for at least about 12 hours, more preferably for at least about 16 hours, and most preferably for up to about 18–24 hours. Preferably, a sustained release tablet releases the active agent from the tablet gradually into the body. For example, a sustained release tablet that is designed to release of the active agent for about 18–24 hours preferably has the following dissolution specification using the dissolution test method described in Example 6A: no more than 40% of the active agent (e.g., by weight) released in 1 hour, about 70–85% of the active agent released in 12 hours, and no less than about 80% of the active agent released at 24 hours. In another example, a sustained release tablet is designed to release the active agent at a nearly linear zero order rate (typically when the active agent dissolution is measured up to 70% of the active agent release).

The "size" of active granules or pellets, or coated beads or coated particles refers to the average dimension and can be measured by either laser diffraction sizer analysis or mechanical siever such as Ro-Tap.

Unless specified otherwise, a range of "molecular weight" of a polymer (e.g., a polyethylene oxide polymer) or a gelation facilitator agent (e.g. a polyethylene glycol) described below is a weighted average molecular weight (measured by gel permeation chromatography).

The term "cps" or "centipoise" is a unit of viscosity =m Pascal second. The viscosity is measured by Broolfield or other viscometers. See, e.g., Wang (1998) *Clin. Hemorheol. Microcirc.* 19:25–31; Wang (1994) *J. Biochem. Biophys. Methods* 28:251–61; Cooke (1988) *J. Clin. Pathol.* 41:1213–1216.

Tablet "hardness" is physical strength measurement of the tablet. The resistance of a tablet to chipping, abrasion, or breakage under conditions of storage, transportation and handling before usage depends on its hardness, or "crushing strength." The tablet "crushing" or "tensile" strength is defined as the force required to break a tablet by compression in the radial direction. It is typically measured using one of the many commonly available tablet hardness testers. For example, "Stokes" and "Monsanto" hardness testers measure the force required to break the tablet when the force generated by a coil spring is applied diametrically to the tablet. A "Strong-Cobb" hardness tester also measures the diametrically applied force required to break a tablet, the force applied by an air pump forcing a plunger against the tablet placed on an anvil. Electrically operated hardness testers, such as the Schleuniger apparatus (also known as a "Heberlein") can be used. See also, TS-50N, Okada Seiko Co., Japan; Bi (1996) *Chem. Pharm. Bull.* (Tokyo) 44:2121–2127. The tablet hardness can be represented by various units, including in the units of kilopounds ("kp").

The "gelation index" or "percent gelation" as used herein represents the percentage of the portion of the tablet which has undergone gelation. The method of calculating the gelation index is not particularly limited but the following calculation method may be mentioned as an example. Using The Pharmacopeia of Japan XII (referred to "JP" hereinafter) Disintegration Test Fluid 2, a gelation test can be carried out by JP Dissolution Test Method 2 (paddle method) at a paddle speed of 25 rpm. The test tablet is moistened for a predetermined time. The test tablets are then taken out at predetermined intervals, the gel layer is removed and the diameter (D obs) of the portion not forming a gel can be measured. From this D obs value, the gelation index (G) can be calculated (see the equation below).

$$\text{Gelation Index } (G, \%) = \left(1 - \frac{(D\ obs)^3}{(D\ ini)^3}\right) \times 100$$

D obs: The diameter of the portion not gelled after initiation of test

D ini: The diameter of the preparation before initiation of test

As an alternative to measuring the diameter of the tablet, other parameters, such as volume, weight or thickness, of the tablet can be measured to calculate a gelation index.

THE DETAILED DESCRIPTION OF THE INVENTION

In one aspect, the invention provides a modified tablet comprising a gel-forming material and at least one particle comprising an active agent, wherein the particle is formulated to modify release of the active agent from the tablet (e.g., the active agent in contact with a coating material). The gel-forming material forms a matrix (i.e., a gel-forming matrix) for the active agent-containing particles in the modified tablet. In some preferred embodiments, the particle comprises an active agent and a coating material on or around the active agent, wherein the coating material modifies the release of the active agent from the tablet. The combination of the gel-forming matrix and the particle comprising a coating material can provide any desired active agent release profile. For example, embodiments of the invention can provide a sustained release of a hydrophilic drug from the tablet for at least 8 hours, preferably up to between about 12–24 hours. Depending on the ultimate use of the tablets, these tablets typically comprise components that are physiologically or pharmacologically acceptable.

The gel-forming material may comprise: (1) a polymer; and (2) a gelation facilitator agent having a solubility higher than about 0.1 gram/ml in water at a temperature of about 20° C. The polymer is water insoluble and contributes to forming a network of materials within the matrix which can swell upon absorbing water. The gelation facilitator agent is a hydrophilic base that draws water into the core of the gel-forming matrix of the tablet, thereby allowing a substantially complete gelation of the entire tablet before the tablet reaches the large intestine. Different forms and/or types of the polymers and the gelation facilitator agent can be used to modify the gelation rate and/or erosion rate of the gel matrix. They can be selected to provide a controlled release pattern of the active agent-containing particles. Other additives can be incorporated to further modify the gelation and/or release pattern of the active agent.

The particle is formulated to further modify the release of the active agent (in particular the hydrophilic agent) from the tablet. Typically, the particle comprises an active agent and a coating material on, and preferably around, the active agent. The active agent can be in any suitable form. In certain embodiments, the active agent can be in the form of a crystal, a granule, or a pellet. These active agent forms may facilitate certain coating processes of the active agents. Moreover, the particle can comprise a single active agent crystal (or granule or pellets) or can comprise a plurality of active agent crystals (or granules or pellets).

In another aspect, the tablets are designed to have pulsatile or delayed onset release profiles. This can be achieved by designing, e.g. a multilayered tablet. Different layers of the multilayered tablet can have different active agents, different amounts of active agents, different forms of active agents, different amounts or kinds of coating materials, different amounts or kinds of gel-forming materials, etc.

Embodiments of the invention are illustrated by referring to the figures. As shown in the figures, active agent-containing particles can be distributed randomly (see, e.g., FIG. 1A) or can be distributed non-randomly (see, e.g., FIGS. 2A–2C).

FIG. 1A illustrates one of many examples of the modified tablet according to an embodiment of the invention. Tablet 101 comprises a plurality of active agent-containing particles 11 and a gel-forming material 10 surrounding the particles. Additional details regarding the active agents and gel-forming materials are described below.

Figure 1B:
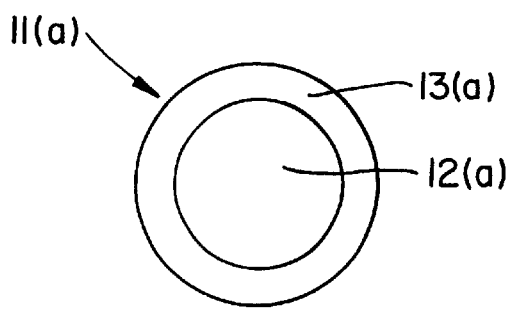
FIG. 1B illustrates an enlarged view of one embodiment of a particle 11(a). The particle 11(a) comprises an active agent 12(a) and a coating material 13(a) on and around the active agent.

FIG. 1B illustrates an enlarged view of an active agent-containing particle 11(*a*). Particle 11(*a*) comprises an active agent 12(*a*) as a core element and a coating material 13(*a*) on and around the active agent 12(*a*).

Figure 1C:
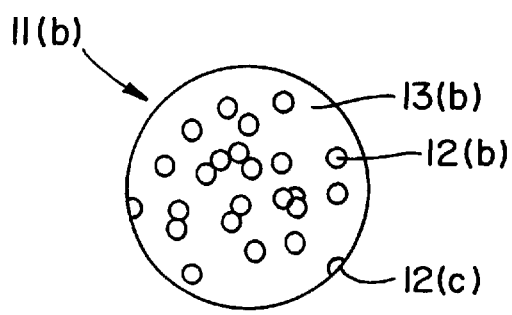
FIG. 1C illustrates an enlarged view of another embodiment of a particle 11(b). The particle 11((b) comprises a plurality of active agents 12(b) and a coating material 13(b) on and around the active agents. The particle 11(b) also comprises a plurality of active agents 12(c), wherein the coating material 13(b) is on, but not necessarily around the active agents.

FIG. 1C illustrates an enlarged view of another example of another active agent-containing particle 11(*b*). Particle 11(*b*) comprises a plurality of active agents 12(*b*) and a coating material 13(*b*) on and around the plurality of active agents 12(*b*). Particle 11(*b*) also comprises a plurality of active agents 12(*c*) and a coating material 13(*b*) on, but not necessary around all of the active agents 12(*c*). As shown in FIG. 1C, the plurality of active agents 12(*b*) and 12(*c*) can be dispersed throughout the coating material 13(*b*).

Figure 2A:
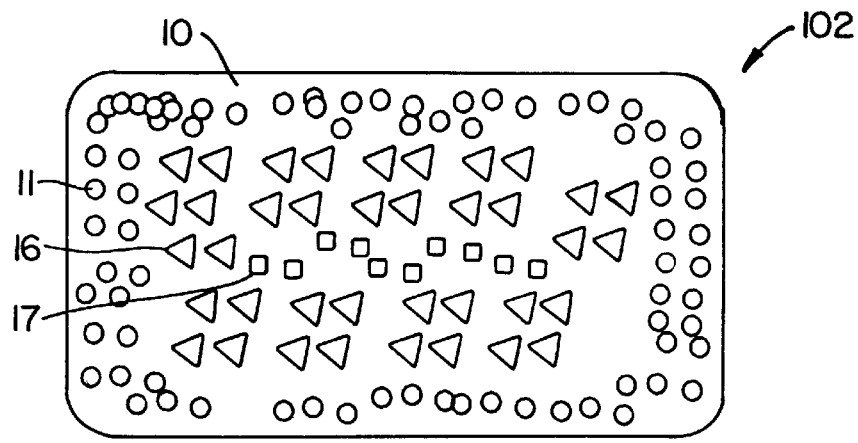
FIG. 2A illustrates another embodiment of tablet 102 comprising a gel-forming matrix 10 and a plurality of different types of particles 11, 16 and 17.

FIG. 2A illustrates another example of a tablet according to an embodiment of the invention. Tablet 102 comprises a plurality of different types of particles 11, 16 and 17 in the gel-forming matrix 10. Each particle may have the same or different form. For instance, the particles 11, 16 and 17 can have the form of either of the previously described particles 11(*a*) or 11(*b*). Particles 11, 16 and 17 can comprise the same active agent but can be differently formulated to have different release properties (e.g., different amounts or different types of coating material). Alternatively, particles 11, 16 and 17 can comprise different types of active agents. For example, the particles 11 near the outer surface of the tablet 102 can be suitable for release into the upper digestive tract, while the particles 16 and 17 in the inner region of the tablet 102 can be suitable for release into the lower digestive tract. Still alternatively, particles 11, 16 and 17 can comprise different amounts or types of active agents or different amounts or types of coating material on them. These particles 11, 16 and 17 can be distributed randomly or can be distributed non-randomly in the tablets.

Figure 2B:
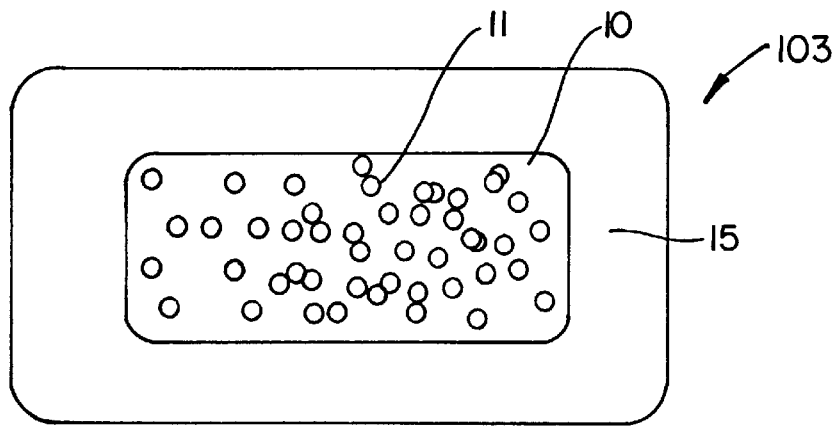
FIG. 2B illustrates an embodiment of multilayered tablet 103 comprising two layers. The core region 10 comprises particles 11 and the outer region 15 is devoid of particles.

FIG. 2B illustrates another example of the tablets according to an embodiment of the invention. Tablet 103 is a multilayered tablet, wherein the core portion 10 comprises particles 11 and the outer portion 15 is devoid of particles. Each portion can comprise different types of gel-forming material to further control the release of the particles comprising an active agent. This type of tablet is particularly useful to delay the onset of release of the active agent from the tablet 103. For example, it may be desirable that a drug only be released in the colon. In this example, the outer portion 15 can erode as the tablet passes through the upper digestive tract. When the tablet reaches the colon, the outer portion has eroded away and erosion of the gel-forming material of the core portion can begin, resulting in the release of the active agent-containing particles into the colon.

Figure 2C:
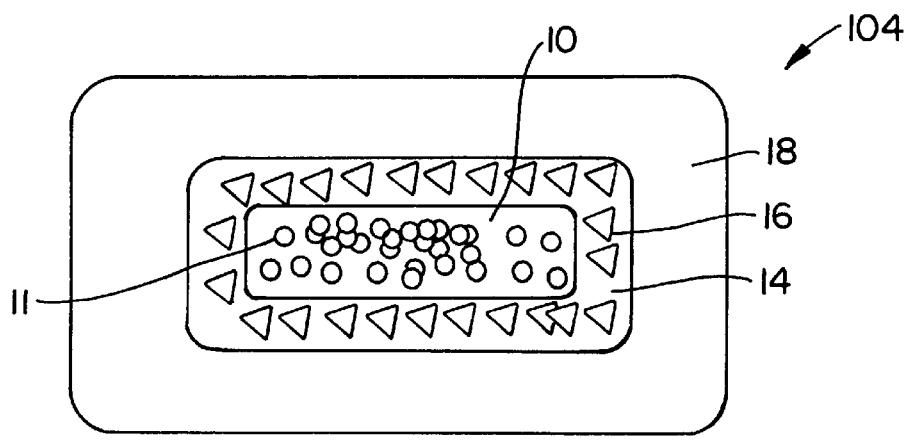
FIG. 2C illustrates another embodiment of multilayered tablet 104 comprising three layers. The core region 10 comprises one type of particles 11, the intermediate region 14 comprises another type of particles 16, and the outer region 18 is devoid of particles.

FIG. 2C illustrates yet another example of a tablet according to an embodiment of the invention. The tablet 104 comprises three layers. The core portion 10 comprises active agent-containing particles 11, the intermediate portion 14 comprises active agent-containing particles 16, and the outer portion 18 is devoid of particles. Particles 11 and 16 can be modified to have different release properties. For example, the particles 11 and 16 can have different amounts or different types of coating material. The particles 11 and 16 can also comprise different types of active agents. Each portion 11, 14 and 18 of the tablet may comprise different amounts or types of gel-forming materials to further control the release of the particles from the tablet.

Embodiments of the invention shown in FIGS. 1 and 2 are merely illustrative, and other variations are readily determinable by those skilled in the art. For example, embodiments of the tablet can further include untreated active agents (e.g., without coating material or in powders) in addition to active agent-containing particles.

I. Active Agents and Pelletization/Granulation Development

Any suitable active agent can be incorporated into the embodiments of the invention. Preferably, the active agent is a drug. However, the active agent is not necessarily limited to a drug, but can be a nutritional additive (e.g., vitamin), a placebo, or a reagent (e.g., a diagnostic reagent, a radioimaging reagent, or a magnetic imaging reagent).

In one embodiment, the active agent is hydrophilic and has a water solubility of at least about 30 mg/ml at a temperature of about 25° C. Optionally, a hydrophilic active agent has a water solubility of at least about 50 mg/ml, at least about 100 mg/ml, at least about 200 mg/ml, at least about 300 mg/ml, at least about 400 mg/ml, at least about 500 mg/ml, at least about 600 mg/ml, at least about 700 mg/ml, at least about 800 mg/ml, at least about 900 mg/ml, at least about 1,000 mg/ml, at least about 1,200 mg/ml, or at least about 1,500 mg/ml at a temperature of about 25° C. Examples of a hydrophilic active agent include, cevimeline HCl, pseudoephedrin HCl, pyrilamine maleate, phenmetrazine HCl, hyoscyamine sulfate, edophonium HCl, doxylamine succinate, hydroxyzine HCl, fluphenazune HCl, niacinamide, etc.

In certain embodiments, the active ingredient of the tablet is (+/−)-cis-2-methylspiro [1,3-oxathiolane-5,3'-quinuclidine]hydrochloride, hemihydrate; also known as SNI-2011, cevimeline hydrochloride, AF102B, SND-5008, and FKS-508. SNI-2011 is a rigid analogue of acetylcholine. See, e.g., Iga (1998) *Jpn. J. Pharmacol.* 78:373–380; Iwabuchi (1994) *Arch. Int. Pharmacodyn. Ther.* 328(3):315–25. It is distributed by, e.g., Snow Brand Milk Product Co., Shinjuku-Ku, Tokyo, Japan. Quinuclidine salt derivative analogues of SNI-2011 can also be used. SNI-2011 and analogues are highly water soluble drugs, having a water solubility of about 1,400 mg/ml at 25° C. Cevimeline hydrochloride has a water solubility of 766 mg/ml at 25° C. They specifically bind to specific muscarinic receptors in various exocrine glands. They have demonstrated beneficial effects on xerostomia and keratoconjunctivitis sicca in patients with Sjogren's syndrome, see, e.g., Iwabuchi (1994) *Gen. Pharmacol.* 25:123–129.

Preferably, the daily dose of these and other drugs that can achieve 18–24 hour extended release is incorporated into the tablet. Typically, about 1 mg to about 500 mg, optionally about 10 mg to about 200mg, optionally 50 mg to about 100 mg, or optionally about 75 mg to about 90 mg of the active agent, e.g., Cevimeline hydrochloride, is incorporated into the tablet. This dosage could accommodate once a day dosing of the active agent. Typically, the weight percent of the active agent itself can be between about 0.5% to about 50% of the total tablet weight.

In another embodiment, an active agent can be non-hydrophilic (e.g., hydrophobic) or can have a water solubility of less than, e.g., 30 mg/ml or 20 mg/ml at a temperature of about 25° C.

In yet another embodiment, an active agent is a drug that is unstable if it is in contact with water or a gel-forming matrix for a prolonged period of time (e.g., sensitive to moisture or oxidation). These active agents may benefit by having a physical and/or chemical barrier (e.g., a coating material) on or around the active agents. Examples of unstable drugs include antibiotic drugs such as efrotomycin, milbemycins, tylosin derivatives, averinectins, ivermectin, mocimycin, goldinomycin, and the like.

Any other suitable active agents can be included in the embodiments of the invention. For example, the active agents include, but are not limited to, e.g., anti-inflammatory, antipyretic, anticonvulsant and/or analgesic agents such as indomethacin, diclofenac, diclofenac Na, codeine, ibuprofen, phenylbutazone, oxyphenbutazone, mepirizol, aspirin, ethenzamide, acetaminophen, aminopyrine, phenacetin, scopolamine butylbromide, morphine, etomidoline, pentazocine, fenoprofen calcium, etc; tuberculostats such as isoniazid, ethambutol hydrochloride, etc.; cardiocirculatory system drugs such as isosorbide dinitrate, nitroglycerin, nifedipine, barnidipine hydrochloride, nicardipine hydrochloride, dipyridamole, arinone, indenolol hydrochloride, hydralazine hydrochloride, methyldopa, furosemide, spironolactone, guanethidine nitrate, reserpine, amosulalol hydrochloride, amitriptyline hydrochloride, neomapride, haloperidol, moperone hydrochloride, perphenazine, diazepam, lorazepam, chlordiazepoxide, diltiazem, ™etc.; antihistaminic agents such as chlorpheniramine maleate, diphenhydramine hydrochloride, etc.; vitamins such as thiamine nitrate, tocopherol acetate, cycothiamine, pyridoxal phosphate, cobamamide, ascorbic acid, nicotinanide, etc.; antigout agents such as allopurinol, colchicine, probenecid, etc.; hypnotic sedatives such as amobarbital, bromovalerylurea, midazolam, chloral hydrate, etc.; antineoplastic agents such as fluorouracil, carmofur, aclarubicin hydrochloride, cyclophosphamide, thiotepa, etc.; anticongestants such as phenylpropanolamine, ephedrine, etc.; antidiabetics such as acetohexamide, insulin, tolbutamide, etc.; diuretics such as hydrochlorothiazide, polythiazide, triamterene, etc.; bronchodilators such as aminophylline, formoterol fumarate, theophylline, etc; antitussives such as codeine phosphate, noscapine, dimemorfan phosphate, dextromethorphan, etc; antiarrhythmic agents such as quinidine nitrate, digitoxin, propafenone hydrochloride, procainamide, etc.; surface anesthetics such as ethyl aminobenzoate, lidocaine, dibucaine hydrochloride, etc.; antiepileptics such as phenytoin, ethosuximide, primidone, etc.; synthetic adrenocortical steroids such as hydrocortisone, prednisolone, triamcinolone, betamethasone, etc.; digestive system drugs such as famotidine, ranitidine hydrochloride, cimetidine, sucralfate, sulpiride, teprenone, plaunotol, etc.; central nervous system drugs such as indeloxazine, idebenone, tiapride hydrochloride, bifemelane hydrochloride, calcium hopantenate, etc.; hyperlipemia treating agents such as pravastatin sodium etc.; and antibiotics such as ampicillin phthalidyl hydrochloride, cefotetan, josamycin and so on. Typical drugs among the above drugs is nicardipine hydrochloride, SNI-2011, nifedipine, ditilazem hydrochloride, phenylpropanolamine hydrochloride, indomethacin, potassium hydrochloride, diazepamtheophylline, verapamil, morphine, and the like.

In the embodiments of the invention, the active agent can be in any suitable form. For example, it can be in the form of a particle, powder, a crystal, a granule (i.e., an aggregate of smaller units of active agent, also referred to as a pellet). Depending on the methods used to coat the active agents to produce a particle, the active agents may be used as purchased (in the form of a powder or a crystal) or may be processed to form active agent granules or pellets. For example, if active agent granules or pellets are spray coated with a coating material to form coated active agent-containing particles, the active agents are preferably granulated or pelletized to improve the chemical or physical characteristics of the active agents for coating processes. For certain coating processes, it may be preferable that active agents are in the form of a granule or a pellet that has relatively high density and hardness, and relatively low brittleness and surface area.

Figure 3:
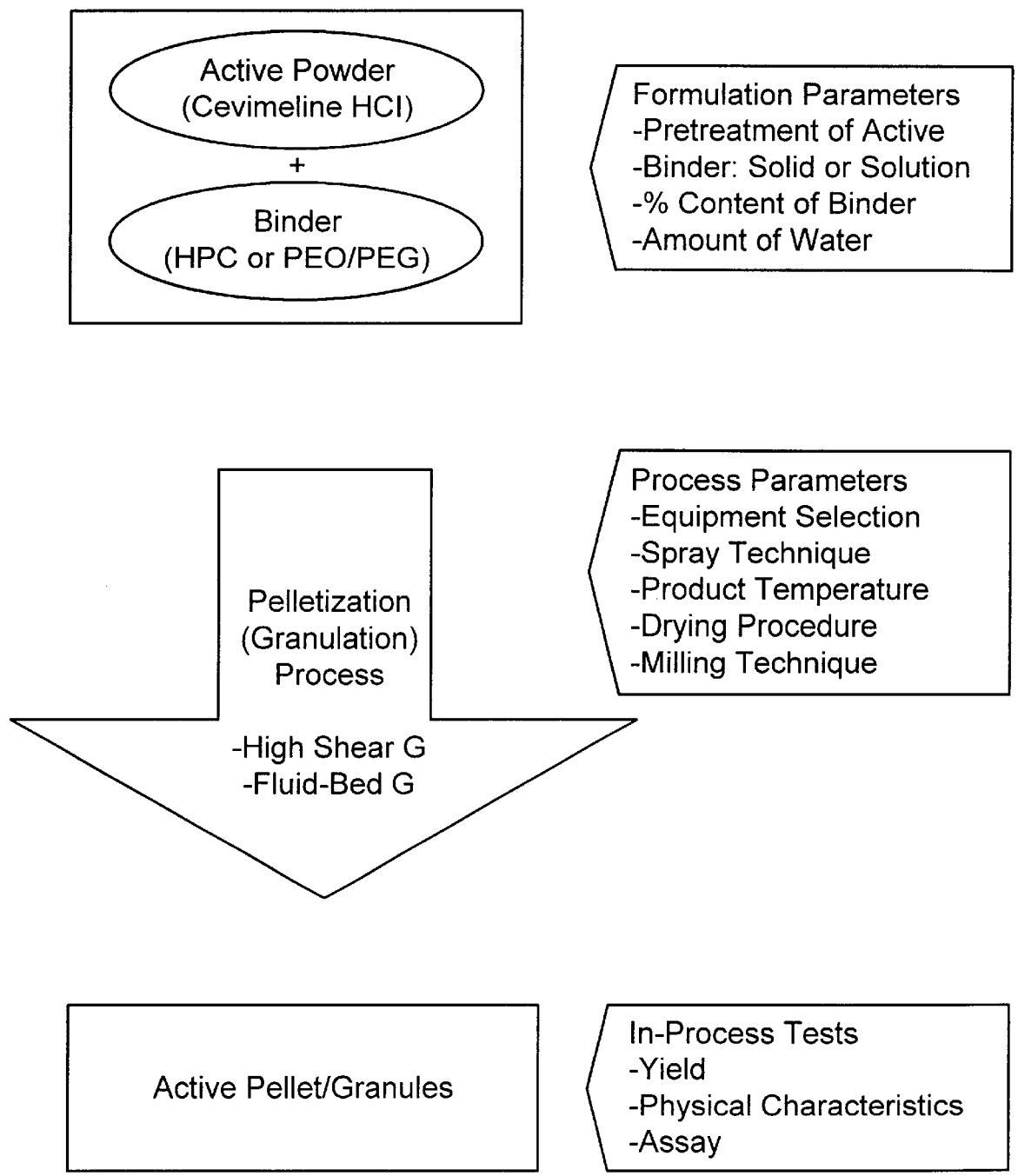
FIG. 3 illustrates an overview of one embodiment of active agent pelletization/granulation development schemes.

An active agent can be pelletized or granulated using any suitable methods known in the art. Pelletization or granulation is commonly defined as a size-enlargement process in which small particles are gathered into larger, permanent aggregates in which the original particles can still be identified. FIG. 3 illustrates one of many examples of an overview of pelletization or granulation development with one embodiment of the active agent (i.e., Cevimeline HCl). Prior to granulation, a binder can be added to the active agent to improve the granulation process. Examples of a suitable binder include, hydroxypropyl cellulose (HPC), a mixture of polyethylene oxide and polyethylene glycol, acacia, carbomer, carboxymethylcellulose sodium, ethylcellulose, dextrin, gelatin, guar gum, hydroxyethyl cellulose, hydroxypropyl methylcellulose, maltodextrin, povidone, pregelatinized starch, zein, starch, and the like. Other additives can be added during granulation. These include, e.g., sweeteners, flavors, color agents, antioxidants, etc.

Optionally, water or other solvent can be added to aid the granulation process. The amount of water or solvent added depends on, e.g. the selection of a granulation process, and is readily determinable by those of skill in the art. Water or other solvent may be added at any suitable time point during the granulation process. For example, a binder may be mixed with a solvent (e.g., water) to form a binder solution, and then the binder solution can be sprayed onto active agents. Alternatively, if a binder solution is too viscous to be uniformly sprayed onto active agents, it may be desirable to blend the binder with the active agent first and then spray water or other solvent to produce uniform pattern of active agent granules or pellets.

Any suitable granulation methods can be used to produce particles comprising an active agent. By definition, granulation is any process of size enlargement whereby small particles are gathered together into larger, permanent aggregates to render them into a free-flowing state. For example, either wet granulation or dry granulation methods can be used.

Dry granulation refers to the granulation of a formulation without the use of heat and solvent. Dry granulation technology generally includes slugging or roll compaction. Slugging consists of dry-blending a formulation and compressing the formulation into a large tablet or slugs on a compressing machine. The resulting tablets or slugs are milled to yield the granules. Roller compaction is similar to slugging, but in roller compaction, a roller compactor is used instead of the tableting machines. See, e.g., *Handbook of Pharmaceutical Granulation Technology*, D. M. Parikh, eds., Marcel-Dekker, Inc. pages 102–103 (1997). Dry granulation technique is useful in certain instances, e.g., when the active agent is sensitive to heat or solvent.

Alternatively, wet granulation can be used. In wet granulation, solvents and binders are typically added to a formulation to provide larger aggregates of granules. The temperature during granulation can be set at any suitable point, generally not exceeding the melting point of any components of the formulation. Typically, the mixture is granulated at a temperature of about 35° C. to about 65° C. for about 20 to 90 minutes. Then the granules are typically air dried for a suitable duration (e.g. one or more hours).

Preferably, the active agents are granulated with high shear mixer granulation ("HSG") or fluid-bed granulation ("FBG"). Both of these granulation processes provide enlarged granules or pellets but differ in the apparatuses used and the mechanism of the process operation. In HSG, blending and wet massing is accomplished by high mechanical agitation by an impeller and a chopper. Mixing, densification, and agglomeration of wetted materials are achieved through shearing and compaction forces exerted by the impeller. The primary function of the chopper is to cut lumps into smaller fragments and aid the distribution of the liquid binder. The liquid binder is either poured into the bowl or sprayed onto the powder to achieve a more homogeneous liquid distribution.

On the other hand, fluidization is the operation by which fine solids are transformed into a fluid-like state through contact with a gas. At certain gas velocities, the fluid will support the particles, giving them freedom of mobility without entrainment. Such a fluidized bed resembles a vigorously boiling fluid, with solid particles undergoing extremely turbulent motion, which increases with gas velocity. Fluidized bed granulation is then a process by which granules are produced in fluidized bed by spraying a binder solution onto a fluidized powder bed to form larger granules. The binder solution can be sprayed from, e.g., a spray gun positioned at any suitable manner (e.g., top or bottom). The spray position and the rate of spray may depend on the nature of the active agent and the binder used, and are readily determinable by those skilled in the art.

These granulation techniques can be performed using commercially available apparatuses. For example, the HSG can be performed using Aeromatic-Field GP1/SP General Processor. Depending on the properties of the active agent, the HSG process is preferred. For example, when Cevimeline HCl was granulated using either HSG or FBG processes, it was found that the HSG process generated the Cevimeline HCl granules or particles of higher density than the FBG process.

Optionally, granulated active agents can be milled. Milling can be performed using any commercially available apparatuses (e.g., Comil equipped with a 0.039 inch screen). The mesh size for the screen can be selected depending on the size of the active agent granule or pellet desired. Typically, the mesh size can range from 0.331 inch screen (mesh 20) to 0.006 inch screen (mesh 100). The milling process aids in providing relatively uniform active agent granules. After the granulated active agents are milled, they may be further dried (e.g., in the air) if desired.

Typically, the mean size of the active agent granule or pellet can range from about 50 μm to about 3 mm, optionally about 100 μm to about 2 mm, or optionally about 300 μm to about 1 mm. Typically, the bulk density or the tap density of the active agent granules or pellets range from about 0.1 g/ml to about 1.5 g/ml, optionally about 0.3 g/ml to about 0.8 g/ml, optionally about 0.4 g/ml to about 0.6 g/ml. Bulk density is measured based on USP method (see *US Pharmacopoeia*, edition XXIV, pages 1913–1914, testing method <616>, incorporated herein by reference).

II. Preparation of Particles Comprising an Active Agent and a Coating Material

Active agents (as purchased or as pelletized) are processed to form a particle with a coating material, wherein the coating material is in contact with the active agents to modify the release of the active agents. For example, the particle comprises an active agent and a coating material on or around the active agent as shown in FIGS. 1B or 1C. Advantageously, this physical/chemical modification of the active agent provides improved sustained or controlled release of active agents from the tablet. Besides controlling active agent release pattern, physical modification of the active agent using encapsulation, granulation, and/or polymer coating techniques has many advantages such as less inter- intra-individual variation, a very reduced influence of gastric emptying and intestinal transit time, reduced influence of pH, viscosity and consequently of food and of the position of the body as well as gastroresistance and tastemasking.

Any suitable coating material may be used with the embodiments of the invention. For example, the coating material can be a natural polymer, a semi-synthetic polymer, or a synthetic polymer. These include, but are not limited to, chitosan, methylcellulose, ethylcellulose, hydroxyethylcellulose, hydroxypropylcellulose hydroxyethylmethylcellulose, hydroxypropylmethylcellulose, cellulose acetate membrane, cellulose acetate butyrate, cellulose acetate propionate, cellulose acetate phthalate, hydroxypropylmethylcellulose phthalate, polyacrylic acid, polyvinyl acetate, poly(vinylacetate phthalate), poly(vinyl alcohol), poly(vinyl pyrrolidone), poly(lactic acid), poly(glycolic acid), poly(lactic/glycolic acid), poly(dimethyl silicone), poly(hydroxyethyl methacrylate), poly(ethylene/vinyl acetate), poly(ethylene/vinyl alcohol), polyamides, polyesters, polyurethanes, polyureas, or a mixture thereof.

In one embodiment, the coating material is less hydrophilic than the active agent so that the coating material inhibits the diffusion of the hydrophilic active agent through the tablet. Typically, a water insoluble or hydrophobic coating material can be used. Examples of a hydrophobic coating material include ethyl cellulose, polymethacrylic polymers, polyvinylacetate, cellulose acetate polymers, etc. In another embodiment, the coating material is flexible so that it is flexible to withstand the compression pressure during the production of compressed tablets. A tablet is generally compressed to a hardness of at least about 2 kp, typically between about 2 kp to about 10 kp. Accordingly, the coating material preferably comprises sufficient flexibility, plasticity, or elasticity so that it does not deform (e.g., crack or break) during the tablet compression of at least about 2 kp. A plasticizer may be included in the coating material to increase the flexibility of the coating material. Examples of a plasticizer include benzyl benzoate, chlorobutanol, dibutyl sebacate, diethyl phthalate, clycerin, mineral oil, polyethylene glycol, sorbitol, triacetin, triethyl citrate, etc. Optionally, a stabilizer, such as acacia, bentonite, cyclodextrins, glyceryl monostearate, propylene glycol, white or yellow wax, Xanthan gum, etc., can be added to a coating material.

Some of these coating materials are in the form of an aqueous polymeric dispersion and are commercially available. For example, these include Surelease® (ethyl cellulose), Eudragit™ RS/NE (polyacrylic polmers) and Kollicoat® SR (polyvinylacetate), etc. Typically, these commercially available coating materials include a plasticizer and/or a stabilizer.

Depending on the selection of a coating method, a single active agent crystal or granule or a plurality of active agent crystals or granules can be coated to form a single particle. For example, with reference to FIG. 1B, the particle 11(a) may comprise a single active agent crystal or granule 12(a) and coating material 13(a) on and around the active agent. These particles can be produced by, e.g., spraying a coating material on an individual active agent crystal or granule. In another example with reference to FIG. 1C, the particle 11(b) may comprise a plurality of active agents (powders, crystals, or granules) 12(b) and 12(c) and coating material 13(b) on or around the active agents. Particles as shown in FIG. 1C can be produced by, e.g. applying the coating material on the active agent powder, crystals or pellets and then chopping (and optionally milling) the coated mixture into particles. The particles comprising the active agent and the coating materials are herein also referred to as beads or coated beads or coated particles.

Any suitable coating methods can be used to produce particles comprising an active agent and a coating material on or around the active agent. For example, either a type A or a type B coating or encapsulation process can be used.

Type A processes include simple or complex coacervation, interfacial polymerization in liquid media, in-liquid drying, thermal and ionic gelation in liquid media, or desolvation in liquid media techniques. In one embodiment of type A processes, a coacervation process can be used. In both simple and complex coacervation processes, the water phase is utilized as the continuous phase (see, e.g., Ertan (1997) *J. Microencapsul.* 14:379–388; Tuncel (1996) *Pharmazie* 51:168–171). In addition, water soluble polymers can be used in the coacervation process. Typical coating or microencapsulating polymers include, e.g., polyamides, polyesters, polyurethanes, and the polyureas and the like.

In another embodiment, the interfacial polymerization process can be used. In this process, two polymeric monomer suspensions are used—a discontinuous phase comprising particles comprising active agents to be encapsulated and a continuous phase for coating films. The two monomers react at the interface between the core and the continuous phase, causing polymerization under controlled process conditions.

In yet another embodiment, a phase separation technique can be used (see, e.g., Mandal (1998) *Drug Dev. Ind. Pharm.* 24:623–629). In this technique, a polymer of discontinuous phase is generally phased out or desolvated from the solvent continuous phase. This polymer of discontinuous phase will deposit around a reservoir such as a liquid droplet or a solid particle as a polymer wall. The polymer can be deposited either by temperature differential, by the introduction of a second polymer, or by the evaporation of the solvent.

Type B processes utilize spray drying, spray chilling, fluidized bed coating, spray drying, pan coating, and spray coating, electrostatic deposition, centrifugal extrusion, spinning disk or rotational suspension separation, polymerization at liquid-gas or solid-gas interface, pressure extrusion or spraying into solvent extraction bath techniques. Pan coating can be utilized for multiple layer coatings of the tablet (see, e.g., Heinamaki (1997) *Pharm. Dev. Technol.* 2:357–364). Fluid bed coating, referred to as Wurster coating, and spray drying techniques can also be utilized for coating the active agent (see, e.g., Jono (1999) *Chem. Pharm. Bull.* (Tokyo) 47:54–63; Miyamoto (1997) *Chem. Pharm. Bull.* (Tokyo) 45:2043–2050).

The selection of a suitable coating process depends on the physical and chemical characteristics of the active agent, the coating material, etc. and is determinable by those skilled in the art. For instance, when a spray system is used to coat the active agents, it may be desirable to use a coating material that does not have a high tack in its formula which could lead to clogging of the nozzle of the spray system.

Any suitable amount of coating material can be applied on the active agent as long as the coating provides sufficient diffusion or protective barrier for the active agent. Typically, about 20% to about 150% of the coating is applied to the active agent granule, wherein the % coating means % ratio (w/w) of the amount of coating polymer used to the amount of active agent granule (and a binder and other materials in the granule). Preferably, about 30% to about 80% of coating is applied. More preferably, about 40% to about 60% of coating is applied.

Depending on the amount of coating material applied, the mean size of the particles can range, e.g., from about 50 μm to about 5 mm, optionally about 100 μm to about 3 mm, or optionally about 300 μm to about 2 mm. Typically, the bulk density or the tap density of these particles are slightly higher than uncoated active agent granules or pellets. For example, the bulk density or the tap density of the particles can range from about 0.1 g/ml to about 5 g/ml, optionally about 0.3 to about 3 g/ml, optionally about 0.5 g/ml to about 1.0 g/ml. Preferably, the particles are round, even, and smooth. Also preferably, the particles are relatively strong and yet flexible.

Any suitable amount of active agent-containing particles can be included into the final formulation. Typically, about 5% to about 60% of active agent-containing particles by weight to the total weight of the tablet are included. The selection of a suitable amount of active agent-containing particles depends on the dosage desired and is readily determinable by those skilled in the art.

III. Gel-forming Material and Combining Gel-forming Material and Active Agent-containing Particles to Produce Tablets The active agent-containing particles are then blended with a gel-forming material, and the final blend is compressed into tablets without damaging the particles. The gel-forming material forms a matrix for the particles and comprises a polymer and a gelation facilitator agent. The polymer provides a structural basis for the matrix of the tablet to swell upon absorbing water. The gelation facilitator agent is a hydrophilic base that draws water into the core of the gel-forming matrix, thereby allowing substantially gelation of the entire tablet. By incorporating the gelation facilitator agent, the gel-forming matrix absorbs water to undergo substantially complete gelation during its stay in the upper digestive tract and moves into the lower digestive tract undergoing constant erosion, continuously releasing the active agent-containing particles.

The polymer in the gel-forming matrix has physical characteristics, inclusive of viscosity in the gelled state, which permits the tablet to retain its shape more or less during its travel down to the lower digestive tract, including the colon, withstanding the contractile forces of the digestive tract associated with the digestion of food. The properties of the polymer depends on its molecular weight, viscosity, etc. The polymer used in the present invention typically has an average molecular weight ranging from about $0.5 \times 10^6$ daltons to $10 \times 10^6$ daltons, more typically ranging from $1 \times 10^6$ daltons to $8 \times 10^6$ daltons. Preferably, the polymer component in the gel-forming material has an average molecular weight of at least about $1 \times 10^6$ daltons and has a viscosity of at least about 1,000 cps in a 1% water solution at a temperature of about 25° C. (i.e., if 1% by weight of PEO is added to water, the aqueous solution containing PEO has a viscosity of at least about 1,000 cps). More preferably, the polymer has an average molecular weight of at least about $2 \times 10^6$ daltons, even more preferably between about $5 \times 10^6$ daltons to about $10 \times 10^6$ daltons. If desired, any mixture of two or more polymers can be used included in the gel-forming material.

Among such polymers are polyethylene oxide (PEO) [e.g., Polyox WRS-303 (average mol. wt.: $7 \times 10^6$; viscosity: 7500–10000 cps, 1% in $H_2O$, 25° C.), Polyox WSR Coagulant (average mol. wt.: $5 \times 10^6$; viscosity: 5500–7500 cps, under the same condition above), Polyox WSR-301 (average mol. wt.: $4 \times 10^6$ Viscosity: 1650–5500 cps, under the same condition above), Polyox WSR-N-60K (average mol. wt.: $2 \times 10^6$; viscosity: 2000–4000 cps, 2% in $H_2O$, 25° C.), all of which are trade names of Union Carbide Co.]; hydroxypropylmethylcellulose (HPMC) [e.g., Metolose 90SH10000 (viscosity: 4100–5600 cps., 1% in $H_2O$, 20° C.), Metolose 90SH50000 (viscosity: 2900–3900 cps, under the same condition above), Metolose 90SH30000 (viscosity: 25000–35000 cps, 2% in $H_2O$, 20° C.), all of which are trade names of Shin-Etsu Chemicals Co.]; sodium carboxymethylcellulose (CMC—Na) [e.g., Sanlose F-150MC (average mol. wt.: $2 \times 10^5$, viscosity: 1200–1800 cps, 1% in $H_2O$, 25°

C.), Sanlose F-1000MC (average mol. wt.: $42 \times 10^4$; viscosity: 8000–12000 cps, under the same condition above), Sanlose F- 300MC (average mol. wt.: $3 \times 10^5$; viscosity: 2500–3000 cps, under the same condition above), all of which are trade names of Nippon Seishi Co., Ltd.]; hydroxyethylcellulose (HEC) [e.g., HEC Daicel SE850 (average mol. wt.: $148 \times 10^4$; viscosity: 2400–3000 cps, 1% in $H_2O$, 25° C.), HEC Daicel SE900 (average mol. wt.: $156 \times 10^4$; viscosity: 4000–5000 cps, under the same condition above), all of which are trade names of Daicel Chemical Industries]; carbonxyvinyl polymers [e.g., Carbopol 940 (average mol. wt.: ca. $25 \times 10^5$; B. F. Goodrich Chemical Co.) and so on.

In a preferred embodiment, a PEO is used as a polymer as part of the gel-forming material. Where a continuous release of the drug over a long time, for example more than 12 hours, is desired, a polymer having a higher molecular weight, preferably an average molecular weight of more than $4 \times 10^6$ daltons, or a higher viscosity, preferably a viscosity of more than 3000 cps at a concentration of 1% in water at 25° C., is preferable.

Another component of the gel-forming material is a gelation facilitator agent. The gelation facilitator agent can be at least one excipient having solubility higher than 0.1 g/ml in water at room temperature (e.g., 20° C.). The gelation facilitator agent allows water to penetrate into the core of the tablet. The higher the solubility of the gelation facilitator agent in water, the more effective it is in allowing into the core of the tablet. Preferably, the gelation facilitator agent has water solubility of at least about 0.2 g/ml, more preferably at least about 0.25 g/ml, most preferably at least about 0.3 g/ml at room temperature (e.g., 20° C.).

Examples of such gelation facilitator agent include highly hydrophilic polymers such as different molecular weight polyethylene glycol (PEG), e.g., polyethylene glycols (PEG), e.g. PEG400, PEG800, PEG1000, PEG1200, PEG1500, PEG2000, PEG4000, PEG6000, PEG8000, PEG10000 and PEG20000, and the like (produced by, e.g., Nippon Oils and Fats Co.), or mixtures thereof. Other highly hydrophilic polymers that can be used as gelation facilitator agents include polyvinylpyrrolidone (PVP; e.g. PVP K30™, PVp K90™ from BASF), hydroxyethylcellulose, hydroxypropylcellulose and the like; sugar alcohols such as D-sorbitol, xylitol, etc.; sugars such as sucrose, anhydrous maltose, D-fructose, dextran (e.g. dextran 40), glucose, etc.; surfactants such as polyoxyethylene-hydrogenated castor oil (HCO; e.g. Cremophor RH40™ produced by BASF, HCO-40™ and HCO-60™ produced by Nikko Chemicals Co.), polyoxyethylene-polyoxypropylene glycol (e.g. Pluronic F68™ produced by Ashai Denka Kogyo K.K.), polyoxyethylene-sorbitan fatty acid ester (Tween; e.g Tween 80 produced by Knato Kagaku K.K.), etc.; salts such as sodium chloride, magnesium chloride, etc.; organic acids such as citric acid, tartaric acid, etc.; amino acids as glycine, β-alanine, lysine hydrochloride, etc.; and amino sugars such as meglumine.

In a preferred embodiment, a PEG is used as a gelation facilitator agent. Typically, a PEG used in the embodiments of the invention has an average molecular weight between about $4 \times 10^2$ daltons and about $2 \times 10^4$ daltons. Preferably, a PEG having an average molecular weight between about 400 daltons to about 1500 daltons is used.

In order to insure that a drug is released into the human colon, it is desired that a portion of the preparation having undergone gelation still remain in the colon even as late as at least 6 to 8 hours, preferably at least 12 hours, after administration. To provide a tablet having such properties, although it depends on the volume of the preparation, the kind of polymer and the properties and amount of the active agent and of the gelation facilitating agent (for insuring a penetration of water into the preparation core), it is generally preferable that the formulation contains about 5 to about 85 weight %, preferably about 20 to about 70 weight %, and more preferably about 40 to about 60 weight % of the gel-forming material (e.g., the polymer and the gelation facilitator agent combined) based on the total weight of the preparation. If the amount of this polymer is less than the above-mentioned level, the preparation may not tolerate erosion in the digestive tract and may not achieve a sustained release of the active agent.

The proportion of the gelation facilitator agent to the polymer depends on the characteristics of the active agent (solubility, therapeutic efficacy, etc.) and content of the active agent, solubility of the gelation facilitator agent itself, characteristics of the polymer used, the patient's condition at the time of administration and other factors. For administration to human patients, however, the proportion of the polymer to the gelation facilitator agent is such that the tablet can achieve a substantially complete gelation in about 4 to 5 hours after administration. Preferably, the amount of the gelation facilitator agent in the tablet is such that the tablet can achieve at least about 70%, preferably at least about 80% gelation or gelation index after two hours according to the gelation test provided in the definition section above (see, also, EP 0 661 045 A1, incorporated herein by reference). When the content of the gelation facilitator agent is too small, the necessary gelation into the core of the preparation does not proceed so that the release of the active agent in the colon becomes insufficient. On the other hand, when the content of the gelation facilitator agent is excessive, the gelation proceeds in a shorter time but the resulting gel becomes so fragile that the release of the active agent is too fast, thus failing to insure a sufficient sustained release.

The ratios of the polymer to gelation facilitator agent are, therefore, generally between about 0.1:99.9 to about 99.9 to 0.1; between about 1:99 to about 99:1 by weight; between about 1:9 to about 9:1 by weight; between about 3:7 to about 7:3 by weight; between about 4:6 to about 6:4 by weight; or between about 3:4 to about 4:3 by weight. Typically, as the proportion of the polymer increases in the formulation, a slower rate of active agent release can be observed. With a specific combination of a polymer (i.e., PEO) and a gelation facilitator agent (i.e., PEG), however, it was observed that there is no further retardation of active agent release when the PEO content increases beyond a PEG:PEO ratio of about 3:4 to about 4:3. The release property of the active agent-containing particles can be manipulated by adjusting the polymer to gelation facilitator agent ratios in the formulation of the tablets.

In certain embodiments, polymers such as hydroxypropylmethylcellulose (HPMC), sodium carboxymethylcellulose (CMC—Na), hydroxyethylcellulose (HEC), carboxyvinyl polymers and the like can be added to the tablet formulation to adjust and thus program the release pattern of the active agent.

If desired, the preparation of the present invention may include appropriate amounts of other pharmaceutically acceptable additives such as vehicles (e.g., lactose, mannitol, potato starch, wheat starch, rice starch, corn starch, and crystalline cellulose), binders (e.g., hydroxypropylmethylcellulose, hydroxypropylcellulose, methylcellulose, and gum arabic), swelling agents (e.g., carboxymethylcellulose and carboxymethylcellulose calcium), lubricants (e.g., stearic acid, calcium stearate, magnesium stearate, talc, magnesium meta-silicate aluminate, calcium hydrogen phosphate, and anhydrous calcium hydrogen phosphate), fluidizers (e.g., hydrous silica, light anhydrous silicic acid, and dried aluminum hydroxide gel), colorants (e.g., yellow iron sesquioxide and iron sesquioxide), surfactants (e.g., sodium lauryl sulfate, sucrose fatty acid ester), coating agents (e.g., zein, hydroxypropylmethylcellulose, and hydroxypropylcellulose), aromas (e.g., l-menthol, peppermint oil, and fennel oil), and preservatives (e.g., sodium sorbate, potassium sorbate, methyl p-benzoate, and ethylbenzoate).

Any suitable methods can be used to mix the formulation comprising the active agent-containing particles and the gel-forming materials (e.g., the polymer and the gelation facilitator). For example, direct compression or granulation (wet or dry) methods can be used.

In one embodiment, the active agent-containing particles and the gel-forming materials are combined, and the mixture may be directly compressed into a tablet. Typically, one or more vehicles or additives may be added to the mixture to improve flow and compressible characteristics. These additives include, for example, lubricants, such as magnesium stearate, zinc stearate, stearic acid, talc and the like, flavors, or sweeteners. Direct compression has advantages, such as reducing cost, time, operational pace and machinery; preventing active agent-excipient interaction and less instability of active agent. Direct blending or slugging can also eliminate the possible pollution by organic solvent.

In another embodiment, a wet granulation process can be used to mix one or more components of the formulation. For example, high shear granulation or fluid-bed granulation processes can be used. Any suitable commercially available granulation apparatuses can be used in these processes.

In yet another embodiment, a dry granulation process can be used to mix one or more components of the formulation. For example, slugging or roller compaction can be used. Both wet and dry granulation processes and apparatuses are described in detail above.

When granulation methods are used, some of the formulation components may be partially granulated prior to compression or all of the formulation components may be granulated prior to compression. For example, some or all components of the gel-forming material can be granulated prior to mixing the active agent-containing particles. In another embodiment, the polymer component (e.g., PEO) of the gel-forming material can be granulated prior to mixing with the gelation facilitator agent and/or with the particles. In yet another embodiment, the gelation facilitator agent of the gel-forming material can be granulated prior to mixing with the polymer and/or the particles. In yet another embodiment, the particles comprising an active agent can be granulated together with the gel-forming material (e.g., the polymer, the gelation facilitator agent, or both). If any of the gel-forming material is granulated first, preferably, the granules of the gel-forming material are soft or flexible enough not to damage the active agent-containing particles during compression.

After the granulation of one or more components of the formulation, optionally, granulated formulation can be milled. Milling can be performed using any suitable commercially available apparatus (e.g., Comil equipped with a 0.039 inch screen). The mesh size for the screen can be selected depending on the size of the granules desired. After the granulated active agents are milled, they may be further dried (e.g., in the air) if desired.

After preparing the formulation as described above, the formulation is compressed into a tablet form. This tablet shaping can be done by any suitable means, with or without compressive force. For example, compression of the formulation after the granulation step can be accomplished using any tablet press, provided that the tablet composition is adequately lubricated. The level of lubricant in the formulation is typically in the range of 0.5–2.0%, with magnesium stearate which is most commonly used as a lubricant. Other lubricants, such as zinc stearate, stearic acid, talc and the like, may also be used. Many alternative means to effect this step are available, and the invention is not limited by the use of any particular apparatus. The compression step can be carried out using a rotary type tablet press. The rotary type tableting machine has a rotary board with multiple throughholes, or dies, for forming tablets. The formulation is inserted into the die and is subsequently press-molded.

The diameter and shape of the tablet depends on the molds, dies and punches selected for the shaping or compression of the granulation composition. Tablets can be discoid, oval, oblong, round, cylindrical, triangular, and the like. The tablets may be scored to facilitate breaking. The top or lower surface can be embossed or debossed with a symbol or letters.

The compression force can be selected based on the type/model of press, what physical properties are desired for the tablets product (e.g., desired hardness, friability, etc.), the desired tablet appearance and size, and the like. Typically, the compression force applied is such that the compressed tablets have a hardness of at least about 2 kp. These tablets generally provide sufficient hardness and strength to be packaged, shipped or handled by the user. If desired, a higher compression force can be applied to the tablet to increase the tablet hardness. However, the compression force is preferably selected so that it does not deform (e.g., crack or break) the active agent-containing particles within the tablet. Preferably, the compression force applied is such that the compressed tablet has a hardness of less than about 10 kp. In certain embodiments, it may be preferred to compress a tablet to a hardness of between about 3 kp to about 7 kp, optionally between about 3 kp to about 5 kp, or about 3 kp.

Typically, the final tablet will have a weight of about 100 mg to about 2000 mg, more typically about 200 mg to about 1000 mg, or about 400 mg to about 700 mg.

If desired, other modifications can be incorporated into embodiments of the tablet. For example, modification of active agent release through the tablet matrix of the present invention can also be achieved by any known technique, such as, e.g., application of various coatings, e.g., ion exchange complexes with, e.g., Amberlite IRP-69. The tablets of the invention can also include or be coadministered with GI motility-reducing drugs. The active agent can also be modified to generate a prodrug by chemical modification of a biologically active compound which will liberate the active compound in vivo by enzymatic or hydrolytic cleavage; etc. Additional layers or coating can act as diffusional barriers to provide additional means to control rate and timing of drug release.

IV. Manufacture of Tablets Comprising Non-randomly Distributed Active Agents

In another aspect, embodiments of the invention provide tablets that comprise non-randomly (e.g., not evenly) distributed active agent-containing particles. By non-randomly distributing the active ingredient (or other formulation substituent) in the body of the tablet, a non-constant, but controlled level of active agent delivery can be achieved. This achieves a "programmable release profile," such as, e.g. a pulsatile or delayed onset release profile. The tablets can also be designed and manufactured such that "lag times" of release are incorporated into this scheme. For example, the tablets can be designed to have a delayed onset release of about 2 hours, about 3 hours, about 4 hours, about 5 hours, about 6 hours, or about 7 hours, after the administration.

In certain embodiments, the non-random active agent-containing distribution is controlled through a multilayer tablet formulation design and manufacturing process. The non-random distribution of active agent can be represented quantitatively by different amounts in different layers or qualitatively by having different forms of active agent in different layers, e.g., as having more coating materials in the particle in the outer layers as compared to the inner layers of the tablet, or, vice versa. For example, alternative layers can have, in addition to varying amounts of active agent, particles comprising the same active agent by different amounts of coating materials or different compositions of coating materials, and the like, or varying amounts of any combination of these alternative forms.

In alternative embodiments, the non-random distribution of the active agent in the tablet is concentrated at the core of the tablet or is concentrated at the periphery of the tablet. In another embodiment, the tablet has multiple layers comprising varying amount of active agent or other formulation ingredients. Varying amounts of active agent can be in different layers of the multilayered tablet, e.g., increasing amounts of active agent in the outer layers as compared to the inner layers, or vice versa. Alternatively, different forms of active agent (e.g., encapsulated, granulated, conjugated) can be in different layers. Completely different types of active agents (e.g., drugs) or combinations thereof can be placed into different layers. The layers can be of varying thickness. Moreover, one tablet can have one, two, three, four, fix, six, seven, eight, nine, ten, or any number of layers, limited only by the desired size of the finished tablet product, the thickness of each layer, the composition of each layer's formulation, the manufacturing process, and the like.

Various "pulsatile release" profiles can be designed by varying the rate at which the tablet dissolves as it passes through the digestive tract. This can be accomplished by manufacturing different layers of the multilayered tablet with different kinds or amounts of polymer, e.g., polymer molecular weights, different polymer to gelation facilitator agent ratios, different manufacturing compression forces, and the like. Thus, in addition to having different amounts or different modifications of active agent in each layer, the layers themselves can be pre-programmed to dissolve at different rates (and thus release active agent in different anatomical compartments) as the tablet passes through the digestive tract.

The manufacture of the varying layers of a multilayered, pulsatile release tablet can be controlled through the compression coating process. A series of feeding devices equal in number to the number of layers to be designed in the tablet is distributed about a rotary disc (this scheme applies for both the direct compression and granulation processes). In operation, each feeding device emits a defined quantity of material into the female dies as the die travel by the feeding device's output valve. Each feeding device has a compressing device directly downstream, as seen in the direction of movement of the female dies. The compressing devices compress the material admitted into the female dies by the respective feeding devices. The compression causes the various layers of material to adhere to one another. Different amount of compressive force can be used for each layer.

When the desired number of layers have been formed, the resulting multilayered compressed tablet is ejected from the female die. Any appropriate apparatus for forming multilayer tablets can be used to make the pulsatile release tablets of the invention. The tablet can be further processed in any suitable manner, e.g., powder layering in coating pans or rotary coaters; dry coating by double compression technique; tablet coating by film coating technique, and the like. See, e.g., U.S. Pat. No. 5,322,655; Remington's Pharmaceutical Sciences Handbook: Chapter 90 "Coating of Pharmaceutical Dosage Forms" (1990).

The following examples are offered by way of illustration, not by way of limitation.

EXAMPLES

Example 1

Pelletization or Granulation of Active Agent

Cevimeline HCl crystals as purchased (from Ishihara Sangyo Kaishe, Ltd., Japan) have the following physical characteristics.

TABLE 1

Physical Characteristics of Cevimeline HCl Powder (As Received)

| | | | | | |
|---|---|---|---|---|---|
| Bulk Density | | ~0.53 g/ml | | | |
| Tap Density (n = 400) | | ~0.84 g/ml | | | |
| Flow (Compressibility Index) | | Poor (CI: ~37%) | | | |
| Physical Strength of Particle | | Relatively Brittle | | | |
| Mean Particle Size | | ~300μ | | | |
| | | (~440μ when screened thru 60 mesh) | | | |
| Particle Size | < Vol. % | 10% | 25% | 50% | 75% | 90% |
| Distribution | Size (μ) | 28 | 123 | 283 | 431 | 569 |

Cevimeline HCl crystals as received were small and brittle, and were not in an optimal condition to be coated uniformly using the Wurster coating process.

To optimize the physical characteristics of Cevimeline HCl crystals for the Wurster coating process, they were pelletized or granulated as shown in FIG. 3. Pelletization with high shear mixer granulation (HSG) and fluid-bed granulation (FBG) were investigated separately. The high shear granulator employed was Aeromatic-Field GP1/SP General Processor. The high shear granulation product was dried on a tray in the air for 1.5 hours and then milled using Comil equipped with a 0.039 inch screen. After milling, the milled pellets/granules were further dried in the air overnight. When fluid-bed granulation was used, the granulator employed was 10-GPCG-1 from Versaglatt. Two different kinds of binders, hydroxypropyl cellulose (HPC) and PEO/PEG, were also tested. The choice of the binders was based on the compatibility with the active agent. In this example, the active agent was pelletized using 10% binder (e.g., HPC) by weight. No other ingredient was added for pelletization.

Many formulation and process parameters were studied in terms of their effect on the physical characteristics (e.g., densities/flow/size/strength) of pelletized products. Generally, the following observations were made when Cevimeline HCl crystals or powders were pelletized or granulated using the process scheme shown in FIG. 3. First, the HSG process generated the Cevimeline HCl pellets/granules of a higher density than the FBG process. The physical properties of Cevimeline HCl pellets or granules were better when HPC was used as a binder compared to using the PEO/PEG mixture as a binder. When the PEO/PEG binder was used, uniform sized pellets were not made but big sized lumps were partly formed. This result may be due to the different wetting behaviors of PEO and PEG.

Moreover, it was observed that when the aqueous binder solution is highly viscous, it may be difficult to achieve a uniform spray pattern. For example, when the HPC was used as a binder, it was found that it was easier to obtain evenly distributed active agent granules when HPC powder and the active agent were blended first and then water was sprayed on to achieve a uniform pattern.

The physical characteristics of the active pellets/granules produced by the HSG process using HPC as a binder were found to have the following features:

TABLE 2

Physical Characteristics of Active Pellets Prepared by HSG (n = 4).

| | | | | | |
|---|---|---|---|---|---|
| Bulk Density | | 0.64 ± 0.01 g/ml | | | |
| Tap Density (n = 400) | | 0.71 ± 0.01 g/ml | | | |
| Flow (Compressibility Index) | | Good (CI: 8–10%) | | | |
| Physical Strength of Particle | | Relatively Strong | | | |
| Mean Particle Size* | | 566μ | | | |
| Particle Size | < Vol. % | 10% | 25% | 50% | 75% | 90% |
| Distribution* | Size (μ) | 290 | 393 | 542 | 716 | 888 |

*These particle size data were obtained from a typical batch of pelletization. Similar results were observed for other batches.

As shown in the above tables, flow and physical strength are greatly improved and mean particle size is greatly increased by the HSG. The particle shape of active pellets was observed to be round using optical microscopy. From the experimental coating trials, it was concluded that the active agent pellets are much better than the active crystals (as purchased) for the Wurster coating process.

The yield of this HSG process was greater than 90%. Each pelletization product was analyzed using an HPLC method to figure out active content. The HPLC assay showed an active content range of 89.5–90.3%, which is virtually identical to the formulated content. This result indicates that the high shear pelletization was well carried out as designed.

Example 2

Coating the Active Agent Pellets or Granules With a Coating Material

Figure 4:
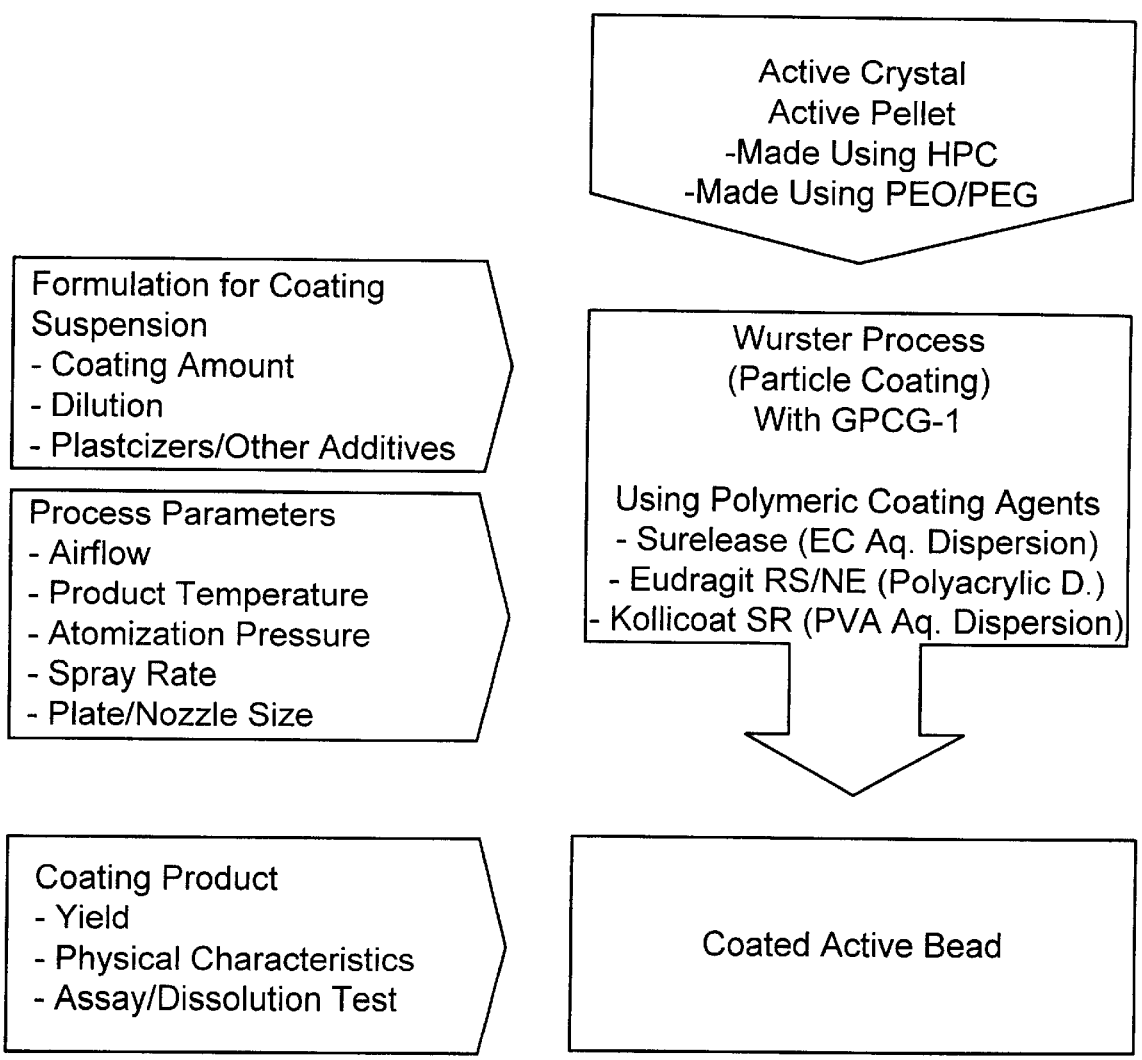
FIG. 4 illustrates one embodiment of coating process schemes to make coated particles or beads comprising active agent pellets or granules.

The active Cevimeline pellets prepared by the HSG process were coated with coating agents using GPCG-1 (230-VG Versa Glatt, screen size 100μ) equipped with Wurster column (diameter 71 mm, partition 1.75 inches). An overview for the coating process development of active pellets is presented in FIG. 4. Three different aqueous polymeric dispersions, Surelease® (ethyl cellulose), Eudragit™ RS/NE (polyacrylic polymers) and Kollicoat® SR (polyvinylacetate), were examined in terms of the ability of each polymer to form hydrophobic flexible coating membrane. Their formulations were also developed to accommodate effective coating process.

Generally, the following observations were made with these three coatings on the Cevimeline pellets. The Wurster coating process for the Cevimeline pellets using Surelease® or Kollicoat® provided a more effective process and a more uniform coating than using Eudragit™ NE or RS as a coating material. Eudragit™ NE or RS had a tendency to stick and agglomerate active agent pellets. Relatively high tack of its formula also led to relatively frequent clogging of the nozzle of spray system.

The following tablets illustrate the formulations developed for the Surelease® and Kollicoat® coating of active agent pellets. The formulation is based on using 50% coating. This % coating means % ratio of the amount of coating polymer by weight used to the amount of active agent pellets given (including HPC). For example, in Table 3,500 grams of active pellets were coated with 1008.1 gram of 24.8% dispersion of Surelease® E-7-19010. Thus, the 50% coating on the active pellets in this example is calculated by multiplying 1008.1 gram by 24.8% (weight of coating polymer), divided by 500 grams (weight of active pellets).

TABLE 3

Formulation for 50% Surelease ® Coating of 500 g Active Pellets As A Typical Example.

| | | | |
|---|---|---|---|
| Surelease ® E-7-19010* (24.8% dispersion) | 1008.1 g | 20.0%** | Coating Polymer |
| DI-Water | 241.9 g | 80.0% | For Dilution to 20% |
| Total | 1250.0 g | 100.0% | |

*This product includes additives (plasticizer/stabilizer, etc.) necessary for coating.
**Dry polymer substance.

TABLE 4

Formulation for 50% Kollicoat ® SR Coating of 500 g Active Pellets As A Typical Example.

| | | | |
|---|---|---|---|
| Kollicoat ® SR 30 D* (30.0% dispersion) | 833.3 g | 20.0%** | Coating Polymer |
| Talc | 12.5 g | 1.0% | Glidant (5% of polymer) |
| DI-Water | 404.2 g | 79.0% | For Dilution to 20% |
| Total | 1250.0 g | 100.0% | |

*This product includes stabilizers, PVP and SLS.
**Dry polymer substance.

The processing parameters were optimized for both coatings. Twenty % (w/w) solid concentration of both the Surelease® and Kollicoat® coating formula (based on the total tablet preparation weight) was found to be most effective for the process. No significant difficulties were observed when both coatings were tried up to 100% coating.

Table 5 illustrates the changes in the physical properties of the Surelease® or Kollicoat® coated active agent-containing particles compared to the physical properites of the active agent pellets without coating (shown in Table 2).

TABLE 5

Changes (Trend) in the Physical Properties of Active Particles after Surelease ® or Kollicoat ® Coating

| | |
|---|---|
| Bulk Density | Increased by ~0.05–0.1 g/ml |
| Tap Density (n = 400) | Slightly Increased by ~0.02–0.8 g/ml |
| Flow | Not Significantly/Slightly Better Flow |
| Compressibility Index | CI: Slightly Decreased by ~2–4% |
| Mean Particle Size | Significantly Increased |
| Particle Shape/Surface | Round and Even/Smooth and Flexible |
| Physical Strength of Particle | Relatively strong and Flexible |

Figure 6:
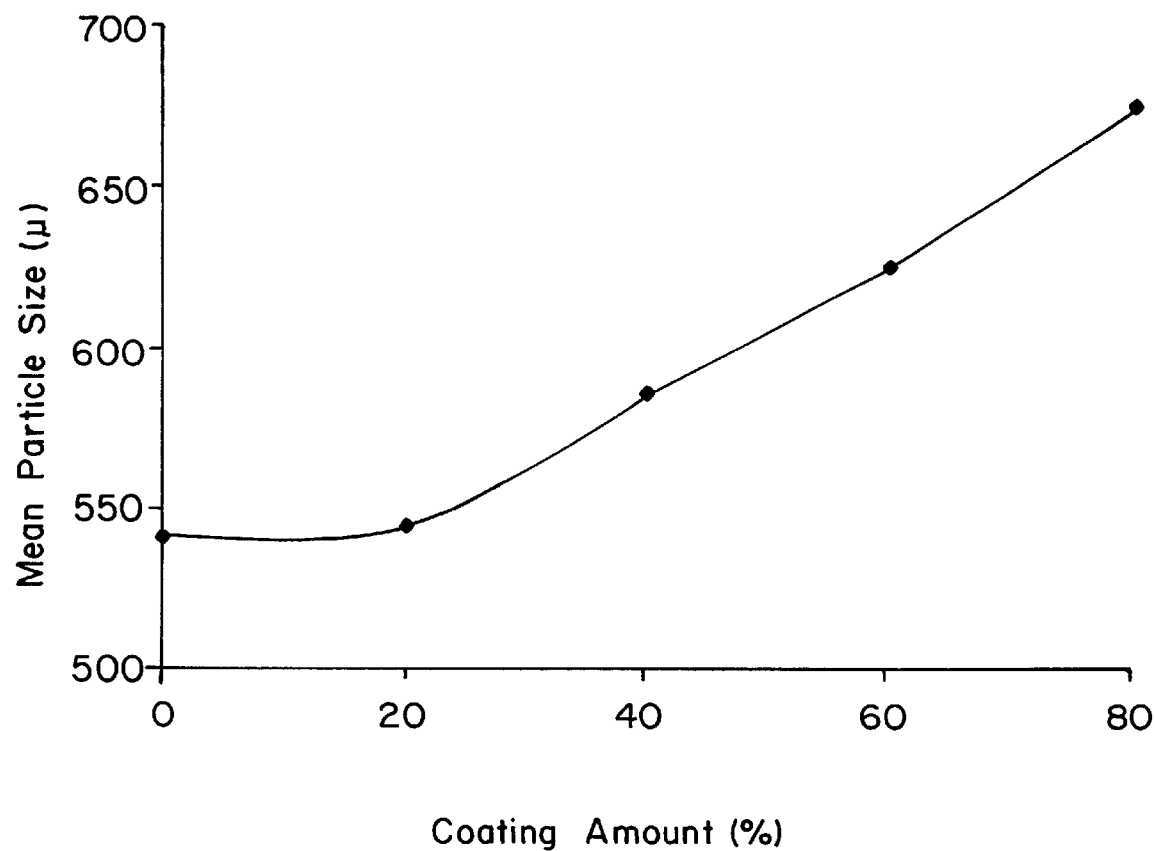
FIG. 6 illustrates a relationship between the amount of coating in particles versus the mean particle size for one embodiment of the invention.

FIG. 6 also shows that mean particle size of coated particles increased substantially as % coating was increased. These results indicate that the particulate coatings were well processed from the viewpoint of physical characteristics. The yield of Wurster process was always higher than 90%.

Example 3

In vitro Dissolution Studies of the Coated Active Agent-containing Particles

In vitro drug release studies for the active agent-containing particles (also referred to as "coated bead" or "coated particle") were carried out using USP II dissolution apparatus (Hanson Research Automated Sampling System) at 75 rpm paddle speed. Coated particle samples were placed into dissolution vessels containing 900 ml of degassed DI water at 37° C. No dissolution medium replacement was made at each sampling but the volume correction was done in calculating drug content. The amount of drug released from bead was measured using an UV-Visible spectrophotometer (Hewlett Packard) at 243 nm.

Figure 7:
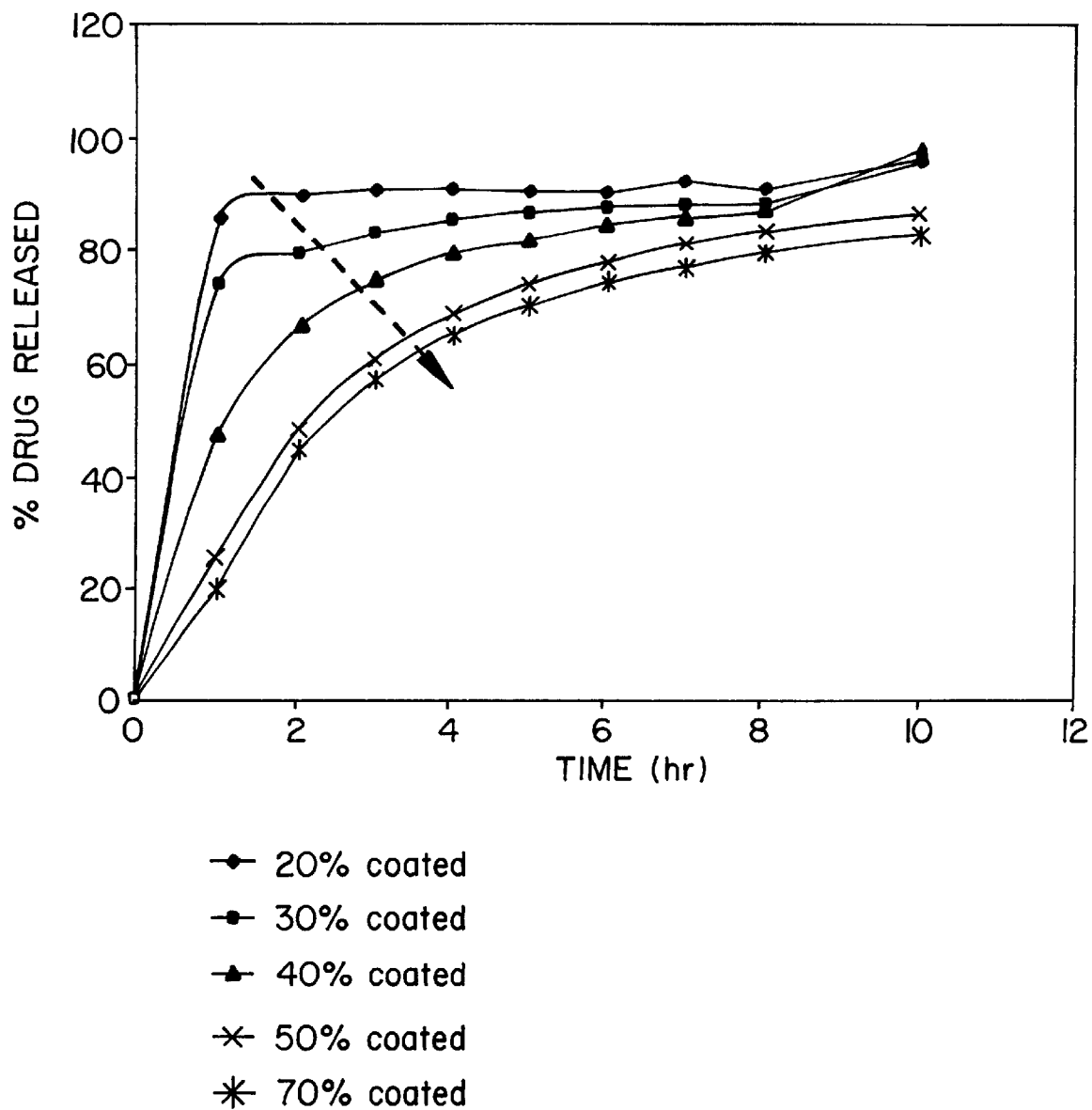
FIG. 7 illustrates the effect of coating amount applied on drug release from the coated particles.

The dissolution profiles of Surelease® coated particles (that are prepared as described above) are presented in FIG. 7. No significant variations were found among the bead samples from a coating batch. These results indicate that the active agent pellets were uniformly and effectively coated. As shown in FIG. 7, the drug release was gradually prolonged as coating amount (% coating) was increased. This implies that the increased % coating results in the increased thickness of the hydrophobic polymeric film. Thus, the drug release rate decreased as the diffusion membrane was thickened. Similar results were observed for Kollicoat® coated particles.

Figure 8:
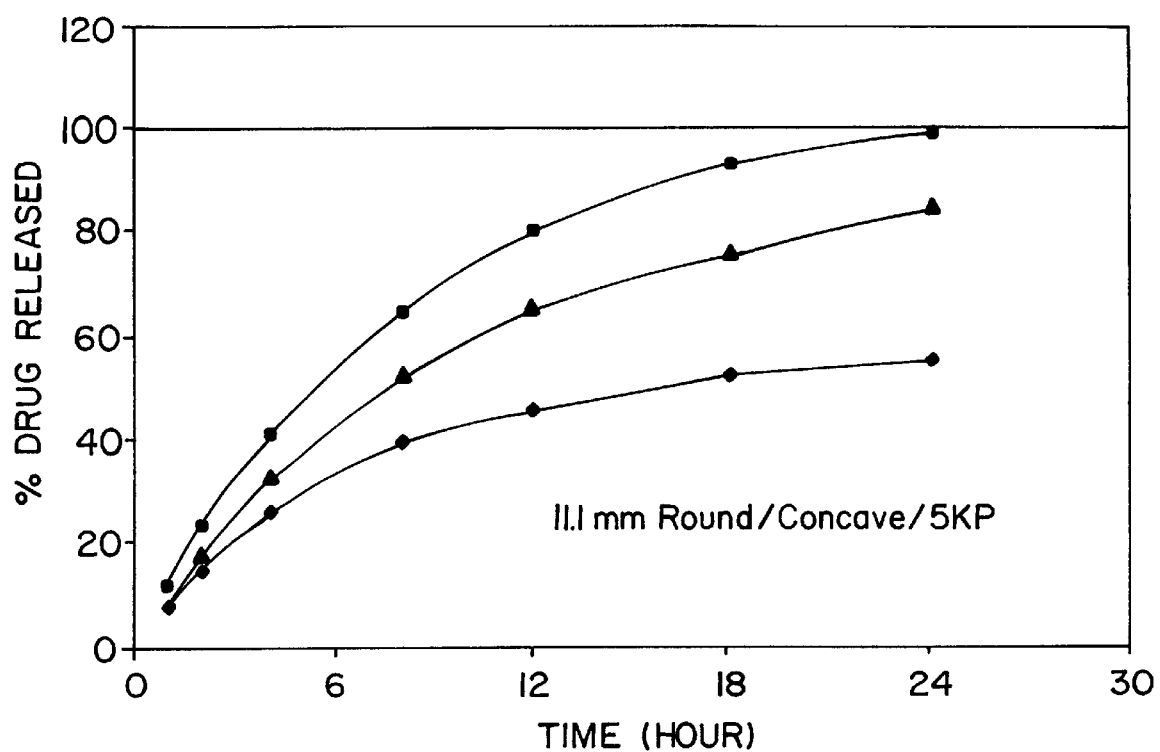
FIG. 8 illustrates drug release profiles from 606 mg tablets comprising 100% Kollicoat® coated particle in the PEO/PEG matrix prepared by fluid-bed granulation (HPLC method, n=3).

However, as shown in FIG. 8, three randomly selected PEO/PEG matrix tablets containing Kollicoat® coated beads showed a significant content non-uniformity. Each of these tablets weighs 606 mg and is 11.1 mm round/concave shaped. Their drug release profiles did not reach 100% up to 24 hours. However, there was a 43.5% deviation in % drug released among the randomly sampled three tablets. Thus, Kollicoat coating may not be an optimal formulation for coating Cevimeline HCl using the Wurster coating process.

Example 4

Gel-forming Matrix Design and Granulation and Compression of PEO/PEG/coated Particles The design of a gel-forming matrix requires several considerations. These include, e.g., how gel-forming material or matrix formers (e.g., a polymer and a gelation facilitator agent) can be effectively prepared, how the matrix formers can be uniformly blended with coated beads, and then how the final blend can be compressed into matrix tablets with no damage of coated beads.

In this example, a polyethylene oxide polymer (i.e., PEO WSR 303 from Union Carbide, Danbury, Conn., USA, MW=7,000,000 daltons) and a polyethylene glycol (i.e., PEG from Union Carbide, Danbury, Conn., USA, MW=8,000 daltons) were used as components of the gel-forming material. Per tablet, 229.0 mg of PEO and 172.0 mg of PEG were used (the PEO/PEG ratio of 4:3 w/w). The physical properties of PEO/PEG powder blend are shown in a following table (n=2):

TABLE 6

Physical Properties of PEO/PEG Powder Blend

| Bulk Density | 0.53 ± 0.001 g/ml |
| Tap Density (n = 400) | 0.59 ± 0.002 g/ml |
| Flow (Compressibility Index) | Good (CI: ~10%) |
| Particle Size | 100–150µ |

The bulk density and particle size of PEO/PEG powder blend are quite different from those of coated particles (see Tables 2 and 5). To achieve uniformity, the PEO/PEG powder mixture was physically modified to have similar physical characteristics to those of the Surelease® or Kollicoat® coated particles. In other words, the bulk density and particle size of the PEO/PEG powder mixture were increased to achieve uniform blending with the coated particles comprising Cevimeline.

The physical modification could be made through dry or wet granulation of PEO/PEG either in the presence or in the absence of coated particles. In the case of the granulation of PEO/PEG with coated particles, the granulation will include a blending procedure. The PEO/PEG granules need to be soft (or flexible) enough not to damage the coated particles during compression. The granules must also serve as a filler of the matrix.

Figure 5:
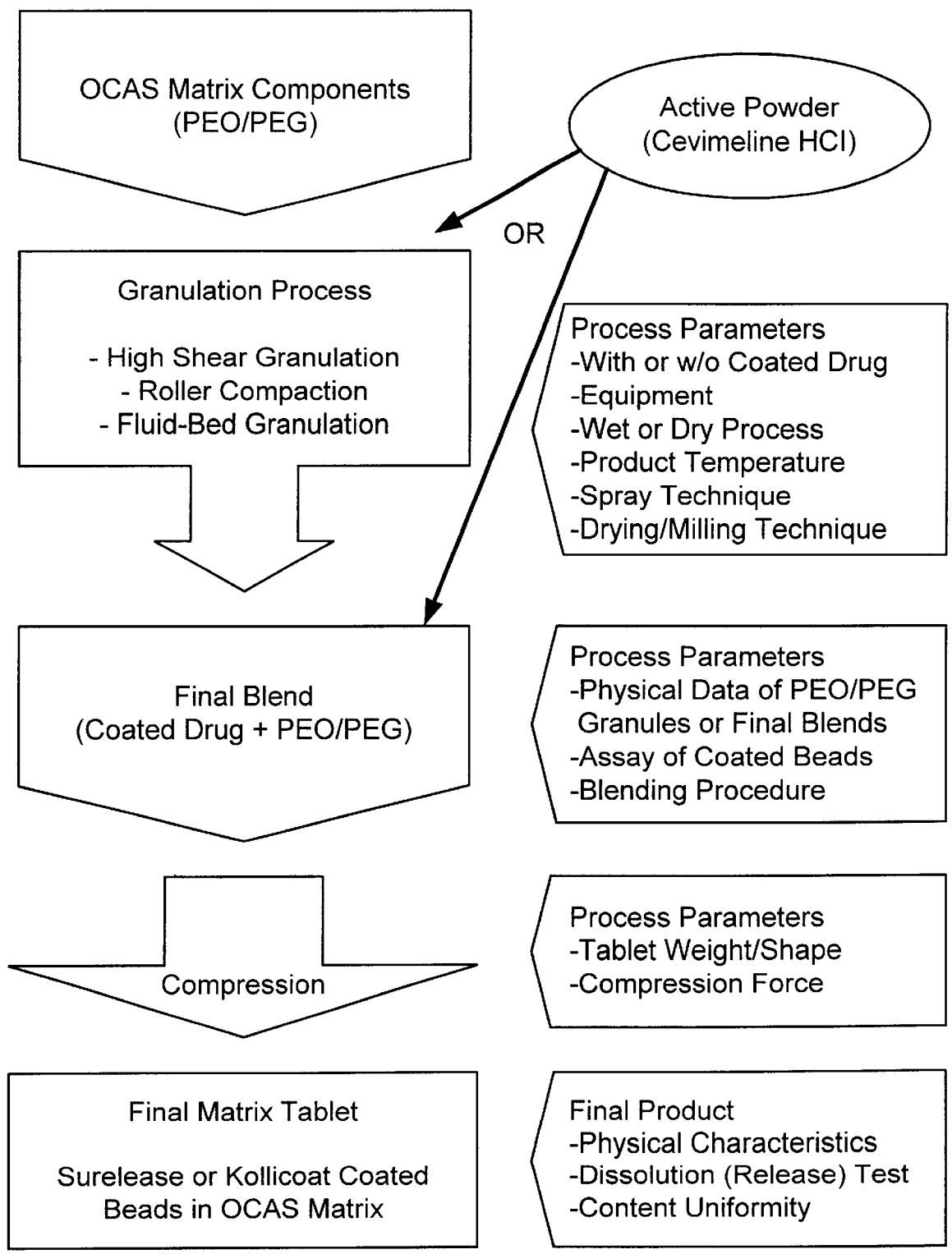
FIG. 5 illustrates an overview of one embodiment of granulation and tabletting processes.

FIG. 5 shows the overview for both the process development of PEO/PEG granulation and the compression of the final blend with coated drug. The physical characteristics for both coated beads and PEO/PEG granules were evaluated in terms of blending uniformity, compressibility and content uniformity of final tablets.

In the initial studies, the following observations were made. The granules generated by HSG looked good-shaped (round) and pretty dense, but were too hard and low in compressibility. Thus, the PEO/PEG granules generated by HSG were not optimal for mixing with the coated particles comprising Cevimeline. The roller compaction dry granulation of PEO/PEG powder resulted in PEO/PEG granules that mixed well with the coated particles comprising Cevimeline. Moreover, the fluid-bed granulation without coated particles generated relatively soft and flexible PEO/PEG granules. However, the granules were too light (approximately half value of bulk density of coated particles). The fluid-bed granulation of PEO/PEG with coated particles was found to be relatively desirable in terms of blending uniformity and compressibility.

A. Roller Compaction Dry Granulation (RCDG)

The roller compaction process of the PEO/PEG powder blend was optimized. The roller compactor used is Fitzpatrick IR 220 Chilsonator. The roller compaction was directly followed by milling. The compacted ribbons were milled using a M5A Fitz Mill equipped with traditional blade rotor and 0.065 inches screen. The characterized properties of the RCDG product are shown in Table 7. The blending between the granules and the Surelease® coated beads was observed to be relatively uniform. The V-blender used is a P-K Blend Master. The formulation is presented in Table 8.

TABLE 7

Physical Characteristics of PEO/PEG Granules Prepared by RCDG (A Typical Case)

| | After Milling | After Screening* |
| --- | --- | --- |
| Bulk Density | 0.51 g/ml | 0.50 g/ml |
| Tap Density (n = 400) | 0.62 g/ml | 0.63 g/ml |
| Compressibility Index | 17% | 21% |
| Physical Strength of Particle | Brittle | Brittle |
| Mean Particle Size* | ~615µ | ~230µ |

*After screened through 30 mesh.

TABLE 8

Tableting Formulation for the Final Blend of Surelease ® Coated Active Beads and PEO/PEG Granules Prepared by RCDG.

| PEO/PEG Granule | 230.0 mg | 56.9% | Matrix Former |
| 70% Surelease Coated Bead* | 170.0 mg | 42.1% | Coated Drug |
| Magnesium Stearate | 4.0 mg | 1.0% | Lubricant |
| Total | 404.0 mg | 100.0% | |

*Theoretically 170 mg of 70% coated active beads have 90 mg of active material, 10 mg of HPC and 70 mg of coating materials.

It was observed that the dissolution profile of Surelease® coated particle in the gel-forming matrix prepared by RCDG did not achieve 18–24 hours extension of drug release. Not wishing to be bound by a theory, this may be due to the possibility that the coated beads were partially damaged by the relatively hard granules made by RCDG.

B. Fluid-bed Wet Granulation with Top-spray Technique (FBG)

GPCG-1 Versa Glatt with top-spray set was used for the fluid-bed granulation of PEO/PEG in the presence of coated drug. A formulation for a given tablet size (606 mg including 1% magnesium stearate) is presented as an example in Table 9. Table 10 lists changes to the physical characteristics after the FBG process. Prior to compression, the FBG product was blended again with the P-K V-blender for 5 minute to increase blending uniformity and mixed with magnesium stearate for additional 2 minutes.

TABLE 9

Formulation for the fluid-bed granulation of PEO/PEG and a 100% Surelease ® coated drug

| | |
|---|---|
| 100% Surelease Coated Bead* | 199.0 mg (90 mg of Active) |
| PEO (Polyox WSR303) | 229.0 mg |
| PEG 8000 | 172.0 mg |
| DI-water** | 20% of total amount of polymers |
| Total | 600.0 mg (Batch Size: 750 g) |

*This 100% Surelease coated bead product was analyzed to be 45.2% by HPLC method (90.0 mg of active/199.0 mg of this bead product).
**Not a finished product ingredient.

TABLE 10

Changes (Trend) in the Physical Properties after the Fluid-Bed Granulation of PEO/PEG and Coated Drug (Compared to Coated Particles)

| | | | | | |
|---|---|---|---|---|---|
| Bulk Density | Decreased (~0.45–0.55 g/ml) | | | | |
| Tap Density (n = 400) | Decreased (~0.53–0.63 g/ml) | | | | |
| Flow | Not Significantly Changed | | | | |
| Compressibility Index | CI: 9–14% | | | | |
| Blending Uniformity | Visually Well-Blended | | | | |
| Appearance of Coated Beads | Visually Not Damaged | | | | |
| Mean Particle Size | Decreased | | | | |
| Particle Size < Vol. % | 10% | 25% | 50% | 75% | 90% |
| Distribution* Size (μ) | 154 | 265 | 458 | 726 | 1071 |

*For a typical case of granulation product

The following observations were made. Relatively fluffy and bouncy PEO/PEG granules smaller than the coated particles were generated separately from the coated particles. Some PEO/PEG granules were adhered to the coated particles to form agglomerates. This led to the most uniform blending between PEO/PEG and coated particles. The blending was most effective and uniform when fluid-bed granulation (with top-spray technique) was used for PEO/PEG in the presence of coated particles.

The change to particle size distribution is evidential enough to back up the above observation. As shown in Table 10, the particle size distribution of the granulation product is wide; bigger and smaller size distributions may represent the agglomerates of PEO/PEG and coated drug and PEO/PEG granules or coated particles only, respectively.

Example 5

Compression of Final Blends

The final blends (those produced by fluid bed granulation by mixing PEO/PEG in the presence of coated particles) were compressed into tablets using PH-106-DMS Korsch rotary tablet press. Three different tablet toolings were individually mounted to the press, depending upon the tablet size and shape designed; 9.5 mm round/concave tooling for 404 mg tablet, 11.1 mm round/concave and 8.7×18.9 mm oval toolings for 606 mg tablet. Different compression forces yielding different hardness were tested to balance two requirements—physical stability of the tablets and minimal damage to the coated particles by the compressive force.

The results from the initial studies were as follows.

First, compression force appears to influence the drug release of the coated bead in matrix dosage form. The Surelease® coated particle containing matrix tablets compressed at 3 kp were more effective in drug release than those at 5 kp or 7 kp. These results may be associated with the safety of coating membrane against the compression force applied and the compactness of matrix by the compression force applied.

Second, tablet shape does not appear to affect drug release significantly.

Third, the total tablet weight appears to influence the drug release profile. In making tablets of varying total tablet weight, the amount of the coated particles was fixed and the amount of the gel-forming material was changed (% content of matrix formers). The PEO:PEG ratio was maintained at 4:3 for all tablets. For instance, the tablet that weighs 404 mg contained 199 mg of active agent-containing particles, 115 mg of PEO, 86 mg of PEG, and 6 mg of magnesium stearate; and the tablet that weighs 606 mg contained 199 mg active agent-containing particles, 229 mg of PEO, 172 mg of PEG, and 6 mg of magnesium stearate. When the tablet weight was changed from 404 mg to 606 mg, the drug release rate was found to decrease over time for the Surelease® coated particles in matrix tablets. For instance, the tablets that weigh 404 mg showed 96% drug release for 12 hours in the case of Surelease® coated particle, while the tablets that weigh 606 mg showed only 83% release.

Example 6

Drug Release from Gel Forming Matrix Tablets: Comparison Between an Untreated Hydrophilic Agent vs. a Treated Hydrophilic Agent A. Dissolution Test Method In vitro drug release studies for these matrix tablets were conducted using USP II dissolution apparatus (Hanson Research SK8 PLUS Auto Plus Maximizer and Autofiller) at 75 rpm paddle speed. Each tablet sample was put into a sinker, and the sinker was then placed into dissolution vessel containing 900 ml of degassed DI water at 37° C. No dissolution medium replacement was made at each sampling but the volume correction was done in calculating drug content. The amount of drug released from matrix tablet was measured using HPLC (Hewlett Packard Series 1100).

B Dissolution Performance of Tablets Comprising Untreated Active Agent

The tablets comprising Cevimeline HCl (Ishihara Sangyo Kaishe, Ltd., Japan) as an active agent without any coating ("conventional" Cevimeline tablets) were manufactured by direct blending the following ingredients: 90mg active agent; PEO WSR 303 (Union Carbide, Danbury, Conn., USA); PEG 8000 (Union Carbide, Danbury, Conn., USA) (PEO/PEG ratio=4:3) and 1% magnesium stearate (Mallinckrodt, St. Louis, Mo., USA) together, then compressing the final blend into tablets that weigh 404 mg using Korsch press. Each tablet contained 90 mg pure untreated active agent, 177 mg of PEO and 133 mg of PEG, and 4 mg of magnesium stearate.

Figure 9:
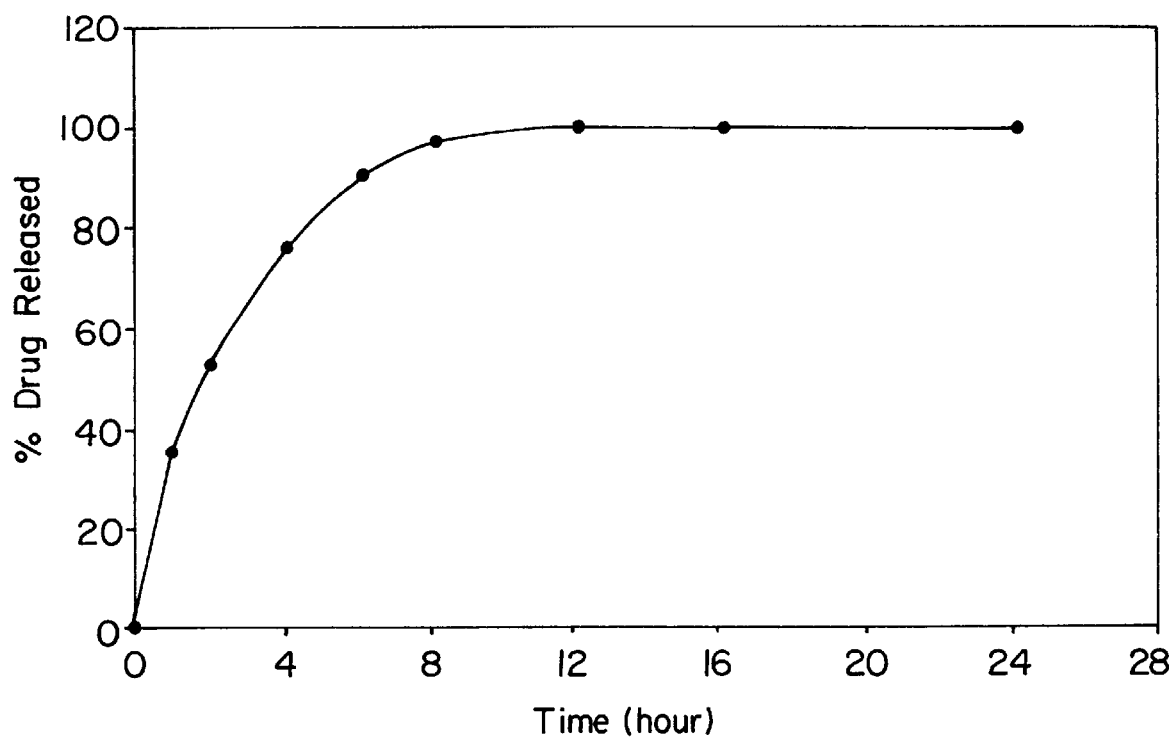
FIG. 9 illustrates drug release profile from conventional Cevimeline HCl-PEO/PEG matrix tablet (HPLC method, n=6).

FIG. 9 illustrates the drug release profile from conventional Cevimeline HCl matrix tablets. As shown in FIG. 9, Cevimeline was released in about 6 hours, and could not achieve 12–24 hour sustained release. This result illustrates that the gel matrix system alone is not sufficient to provide a sustained release of a hydrophilic active agent for up to 12–24 hours.

C. Dissolution Performance of Tablets Comprising Coated Particles

Figure 10:
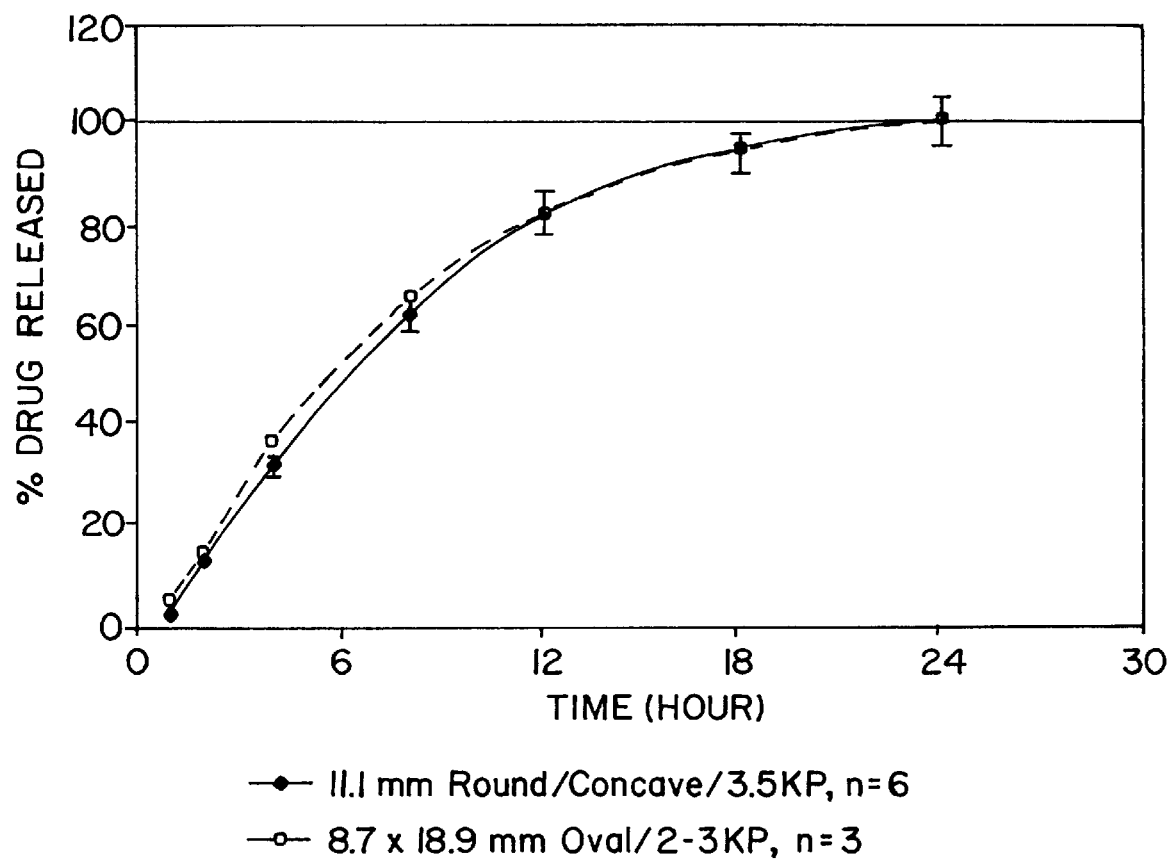
FIG. 10 illustrates release profiles from two different shaped 606 mg tablets composed of 100% Surelease® coated particles in PEO/PEG matrix prepared by fluid-bed granulation (HPLC method).

FIG. 10 illustrates the drug release profiles from two different shaped 606 mg tablets comprising 100% Surelease® coated particles in PEO/PEG gel-forming matrix prepared by fluid-bed granulation (HPLC Method). One set of tablets were round/concave and were 11.1 mm in their dimension. The two different shaped tablets were made using the same batch of 100% Surelease coating. The other set of tablets were oval and were 8.7×18.9 mm in dimension. As shown in FIG. 10, both round and oval shaped tablets had 24 hours sustained drug release in water at 37° C. No significant difference in drug release profile was found between the round and oval tablets.

The deviation among the drug release profiles for both kinds of tablets was observed to be very small. The maximum standard deviation was 5.1% in % drug release. This result indicates that the content uniformity is acceptable, which is consistent with the blending uniformity verified through visual observation.

Therefore, the 100% Surelease® coated particle in the gel-forming matrix dosage form provides 18–24 hours extended release of Cevimeline HCl. Moreover, the results meet a desirable dissolution specification, wherein no more than 40% released at 1 hour, 75±15% released at 12 hours, and no less than 80% released at 24 hours.

Example 7

Manufacture and Testing of Tablets Containing Cardiazem at the Core

This example demonstrates that tablets of the invention incorporating Cardizem SR pellets (diltiazem hydrochloride; Hoechst Marion Roussel) in the core of tablet produce an in vivo delayed release (delayed dissolution) profile.

The tablets were compressed using Carver press with ⅜ inch concave punches and dies by direct compression. First, a layer of PEO/PEG mixture (PEO/PEG ratio=4:3) was placed in the die. Second, Cardizem SR pellets were manually placed on top of the first layer in the core region of the mixture. Third, another layer of PEO/PEG mixture was then put on top of the pellets to maintain the active agent-containing pellets in the core region. Finally, the tablet was compressed with the pellets in the core.

In vitro drug release studies were carried out using the USP apparatus II as described above and using the USP apparatus II at a paddle speed of 100 rpm in 500 ml dissolution medium at 37° C. Samples were assayed using a UV-VIS spectrophotometer at a wavelength of 210 nm.

Figure 11:
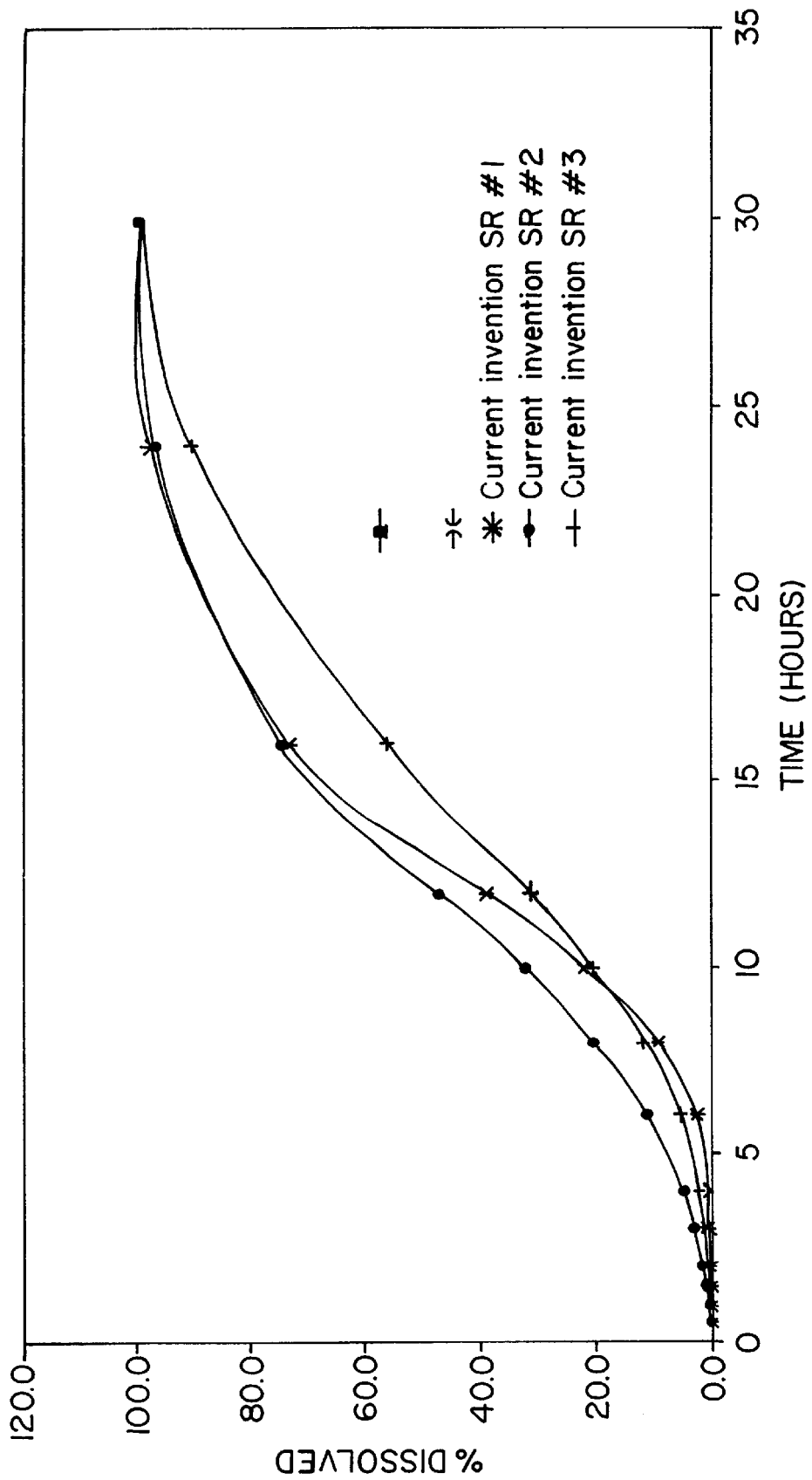
FIG. 11 illustrates dissolution profiles of tablets comprising SR pellets in the core of the tablet.

As shown in FIG. 11, an approximately 5 hours delay of onset of drug dissolution was observed with the Cardizem SR pellets in core of this tablet.

The present invention provides novel materials and methods for producing tablets. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A tablet comprising:
    at least one particle comprising a hydrophilic active agent in contact with a coating material; and
    a gel-forming material comprising:
        a polymer; and
        a gelation facilitator agent having a solubility higher than about 0.1 gram/ml in water at a temperature of about 20° C., wherein said at least one particle is blended with said gel-forming material.

2. The tablet of claim 1, wherein the at least one particle comprises the active agent and said coating material on or around the active agent.

3. The tablet of claim 1, wherein the hydrophilic active agent has a water solubility of at least about 30 mg/ml at a temperature of about 25° C.

4. The tablet of claim 1, wherein the at least one particle has a size between about 50 μm to about 5 mm.

5. The tablet of claim 1, wherein the at least one particle has a size between about 100 μm to about 3 mm.

6. The tablet of claim 1, wherein the at least one particle has a size between about 300 μm to about 2 mm.

7. The tablet of claim 1, wherein the at least one particle is a plurality of particles.

8. The tablet of claim 1, wherein the tablet comprises a plurality of the particles and wherein the gel-forming material forms a matrix for the plurality of the particles.

9. The tablet of claim 1, wherein the active agent is in the form of a crystal or a granule.

10. The tablet of claim 9, wherein the at least one particle comprises a plurality of active agent crystals or granules.

11. The tablet of claim 2, wherein the coating material slows release of the active agent from the tablet when compared to a tablet without the coating material.

12. The tablet of claim 2, wherein the coating material is flexible so that it does not crack during a tablet compression of at least 2 kp.

13. The tablet of claim 2, wherein the coating material is selected from the group consisting of a natural polymer, a semi-synthetic polymer, and a synthetic polymer.

14. The tablet of claim 12, wherein the coating material is a member selected from the group consisting of chitosan, methylcellulose, ethylcellulose, hydroxyethylcellulose, hydroxypropylcellulose hydroxyethylmethylcellulose, hydroxypropylmethylcellulose, cellulose acetate membrane, cellulose acetate butyrate, cellulose acetate propionate, cellulose acetate phthalate, hydroxypropylmethylcellulose phthalate, polyacrylic acid, polyvinyl acetate, poly (vinylacetate phthalate), poly(vinyl alcohol), poly(vinyl pyrrolidone), poly(lactic acid), poly(glycolic acid), poly (lactic/glycolic acid), poly(dimethyl silicone), poly (hydroxyethyl methacrylate), poly(ethylene/vinyl acetate), poly(ethylene/vinyl alcohol), or a mixture thereof.

15. The tablet of claim 11, wherein the coating material further comprises a plasticizer, a stabilizer, or both.

16. The tablet of claim 1, wherein the polymer comprises a polyethylene oxide polymer.

17. The tablet of claim 1, wherein the gelation facilitator agent comprises a polyethylene glycol.

18. The tablet of claim 1, wherein the polymer to the gelation facilitator agent ratio is between about 1:9 to about 9:1 by weight.

19. The tablet of claim 1, wherein the polymer to the gelation facilitator agent ratio is between about 3:7 to about 7:3 by weight.

20. The tablet of claim 1, wherein the polymer to the gelation facilitator agent ratio is between about 4:6 to about 6:4 by weight.

21. The tablet of claim 1, wherein the tablet has a hardness of at least about 2 kp.

22. The tablet of claim 1, wherein the tablet has a hardness of between about 2 kp and about 10 kp.

23. The tablet of claim 1, wherein the tablet provides a sustained release of the active agent for at least about 12 hours.

24. The tablet of claim 1, the tablet further comprising a non-hydrophilic active agent.

25. The tablet of claim 2, wherein the tablet comprises at least two different types of particles with different active agents.

26. The tablet of claim 25, wherein the at least two particles comprise different coating materials.

27. The tablet of claim 7, wherein the distribution of the plurality of particles in the tablet is non-random.

28. The tablet of claim 1, wherein the tablet is a multi-layered tablet.

29. The tablet of claim 7, wherein at least two of the layers of the multilayered tablet comprise a different amount of the plurality particles or at least two different types of active agents.

30. The tablet of claim 7, wherein said tablet has a core and the plurality of particles is concentrated at the core of the tablet.

31. The tablet of claim 30, wherein the tablet provides a delay on the onset of release of the active agent for at least about 2 hours.

32. The tablet of claim 1, wherein the polymer comprises a polyethylene oxide polymer and wherein the gelation facilitator agent comprises a polyethylene glycol.

33. The tablet of claim 32, wherein the tablet provides a sustained release of the active agent for at least about 12 hours.

34. A method for producing a tablet, the method comprising:
   (1) mixing a formulation comprising:
      (a) at least one particle comprising a hydrophilic active agent in contact with a coating material;
      (b) a polymer; and
      (c) a gelation facilitator agent having a solubility higher than about 0.1 gram/ml in water at a temperature of about 20° C., wherein said at least one particle is blended with said gel-forming material; and
   (2) compressing the formulation to produce the tablet.

35. The method of claim 34, wherein the at least one particle is a plurality of particles.

36. The method of claim 34, wherein the at least one particle comprises the active agent and the coating material on the active agent.

37. The method of claim 34, wherein the active agent has a water solubility of at least about 30 mg/ml at a temperature of about 25° C.

38. The method of claim 34, wherein the active agent is in the form of a crystal or a granule.

39. The method of claim 38, wherein the at least one particle comprises a plurality of active agent crystals or active agent granules.

40. The method of claim 34, wherein the at least one particle comprises a plurality of the particles and wherein the gel-forming material forms a matrix for the plurality of the particles.

41. The method of claim 36, wherein the coating material is a member selected from the group consisting of chitosan, methylcellulose, ethylcellulose, hydroxyethylcellulose, hydroxypropylcellulose hydroxyethylmethylcellulose, hydroxypropylmethylcellulose, cellulose acetate membrane, cellulose acetate butyrate, cellulose acetate propionate, cellulose acetate phthalate, hydroxypropylmethylcellulose phthalate, polyacrylic acid, polyvinyl acetate, poly(vinylacetate phthalate), poly(vinyl alcohol), poly(vinyl pyrrolidone), poly(lactic acid), poly(glycolic acid), poly(lactic/glycolic acid), poly(dimethyl silicone), poly(hydroxyethyl methacrylate), poly(ethylene/vinyl acetate), poly(ethylene/vinyl alcohol), or a mixture thereof.

42. The method of claim 36, wherein the at least one particle is produced by spraying the coating material on the active agent.

43. The method of claim 36, wherein the coating material is flexible so that it does not crack during a tablet compression of at least 2 kp.

44. The method of claim 36, wherein the coating material is hydrophobic.

45. The method of claim 43, wherein the coating material further includes a plasticizer, a stabilizer, or both.

46. The method of claim 34, wherein the polymer is a polyethylene oxide polymer.

47. The method of claim 34, wherein the gelation facilitator agent is a polyethylene glycol.

48. The method of claim 34, wherein in step (1), the polymer is granulated with the gelation facilitator agent.

49. The method of claim 34, wherein in step (1), the polymer and the gelation facilitator agent are granulated with the at least one particle.

50. The method of claim 34, wherein the tablet is compressed to a hardness of at least about 2 kp.

51. The method of claim 34, wherein the tablet is compressed to a hardness of between about 2 kp to about 10 kp.

52. The method of claim 35, wherein the plurality of particles are non-randomly distributed throughout the tablet.

53. The method of claim 34, wherein the tablet is multi-layered.

* * * * *